US009974650B2

(12) United States Patent
Nguyen-Thien-Nhon et al.

(10) Patent No.: US 9,974,650 B2
(45) Date of Patent: May 22, 2018

(54) PROSTHETIC HEART VALVE

(71) Applicant: Edwards Lifesciences Corporation, Irvine, CA (US)

(72) Inventors: Diana Nguyen-Thien-Nhon, Irvine, CA (US); Timothy A. Geiser, Laguna Niguel, CA (US); Larry L. Wood, Corona Del Mar, CA (US); Dinesh L. Sirimanne, Irvine, CA (US); Son Nguyen, Irvine, CA (US); Tamir S. Levi, Zichron Ya'acov (IL); Nikolay Gurovich, Hadera (IL); Michael Bukin, Haifa (IL)

(73) Assignee: Edwards Lifesciences Corporation, Irvine, CA (US)

( * ) Notice: Subject to any disclaimer, the term of this patent is extended or adjusted under 35 U.S.C. 154(b) by 0 days. days.

(21) Appl. No.: 15/209,642

(22) Filed: Jul. 13, 2016

(65) Prior Publication Data
US 2017/0014229 A1    Jan. 19, 2017

Related U.S. Application Data

(60) Provisional application No. 62/192,515, filed on Jul. 14, 2015.

(51) Int. Cl.
*A61F 2/24*    (2006.01)

(52) U.S. Cl.
CPC .... *A61F 2/2418* (2013.01); *A61F 2220/0075* (2013.01); *A61F 2230/0026* (2013.01);
(Continued)

(58) Field of Classification Search
CPC ............ A61F 2/2418; A61F 2220/0075; A61F 2230/0026; A61F 2230/0093; A61F 2250/0069; A61F 2/24; A61F 2250/003
See application file for complete search history.

(56) References Cited

U.S. PATENT DOCUMENTS 3,365,728 A    1/1968    Edwards et al.
3,725,961 A    4/1973    Magovern et al.
(Continued)

FOREIGN PATENT DOCUMENTS

AU    2002212418 B2    3/2006
DE    19532846 A1    3/1997
(Continued)

OTHER PUBLICATIONS

H.R. Andersen, et al. "Transluminal Implantation of Artificial Heart Valve. Description of a New Expandable Aortic Valve and Initial Results with implantation by Catheter Technique in Closed Chest Pig," European Heart Journal, No. 13. pp. 704-708. 1992.
(Continued)

*Primary Examiner* — Thomas J Sweet
*Assistant Examiner* — Seema Mathew
(74) *Attorney, Agent, or Firm* — Klarquist Sparkman, LLP; AnneMarie Kaiser

(57) ABSTRACT

An implantable prosthetic valve can comprise an annular frame comprising an inflow end and an outflow end and being radially collapsible and expandable between a radially collapsed configuration and a radially expanded configuration, the frame defining an axial direction extending from the inflow end to the outflow end, a leaflet structure positioned within the frame and secured thereto, and an annular outer skirt positioned around an outer surface of the frame, wherein the outer skirt comprises an inflow edge secured to the frame at a first location, an outflow edge comprising a plurality of alternating projections and notches, wherein the projections are secured to the frame at a second location, and the notches are not directly secured to the frame, an intermediate portion between the inflow edge and the outflow edge that comprises a plurality of openings.

23 Claims, 11 Drawing Sheets

(52) U.S. Cl.
CPC ............... *A61F 2230/0093* (2013.01); *A61F 2250/0069* (2013.01)

(56) References Cited

U.S. PATENT DOCUMENTS

| | | |
|---|---|---|
| 3,755,823 A | 9/1973 | Hancock |
| 3,983,581 A | 10/1976 | Angell et al. |
| 4,035,849 A | 7/1977 | Angell et al. |
| 4,777,951 A | 10/1988 | Cribier et al. |
| 4,787,899 A | 11/1988 | Lazarus |
| 4,796,629 A | 1/1989 | Grayzel |
| 4,856,516 A | 8/1989 | Hillstead |
| 4,878,495 A | 11/1989 | Grayzel |
| 4,966,604 A | 10/1990 | Reiss |
| 4,994,077 A | 2/1991 | Dobben |
| 5,059,177 A | 10/1991 | Towne et al. |
| 5,192,297 A | 3/1993 | Hull |
| 5,258,023 A | 11/1993 | Reger |
| 5,282,847 A | 2/1994 | Trescony et al. |
| 5,370,685 A | 12/1994 | Stevens |
| 5,411,552 A | 5/1995 | Andersen et al. |
| 5,476,506 A | 12/1995 | Lunn |
| 5,545,214 A | 8/1996 | Stevens |
| 5,554,185 A | 9/1996 | Block et al. |
| 5,558,644 A | 9/1996 | Boyd et al. |
| 5,584,803 A | 12/1996 | Stevens et al. |
| 5,591,195 A | 1/1997 | Taheri et al. |
| 5,607,464 A | 3/1997 | Trescony et al. |
| 5,628,786 A | 5/1997 | Banas et al. |
| 5,665,115 A | 9/1997 | Cragg |
| 5,693,088 A | 12/1997 | Lazarus |
| 5,755,783 A | 5/1998 | Stobie et al. |
| 5,769,812 A | 6/1998 | Stevens et al. |
| 5,769,882 A | 6/1998 | Fogarty et al. |
| 5,776,188 A | 7/1998 | Shepherd et al. |
| 5,800,508 A | 9/1998 | Goicoechea et al. |
| 5,840,081 A | 11/1998 | Andersen et al. |
| 5,843,161 A | 12/1998 | Solovay |
| 5,843,179 A | 12/1998 | Vanney et al. |
| 5,855,597 A | 1/1999 | Jayaraman |
| 5,855,601 A | 1/1999 | Bessler et al. |
| 5,925,063 A | 7/1999 | Khosravi |
| 5,957,949 A | 9/1999 | Leonhardt et al. |
| 6,015,431 A | 1/2000 | Thornton et al. |
| 6,027,525 A | 2/2000 | Suh et al. |
| 6,110,198 A | 8/2000 | Fogarty et al. |
| 6,168,614 B1 | 1/2001 | Andersen et al. |
| 6,206,911 B1 | 3/2001 | Milo |
| 6,221,091 B1 | 4/2001 | Khosravi |
| 6,245,102 B1 | 6/2001 | Jayaraman |
| 6,302,906 B1 | 10/2001 | Goicoechea et al. |
| 6,306,164 B1 | 10/2001 | Kujawski |
| 6,352,554 B2 | 3/2002 | De Paulis |
| 6,425,916 B1 | 7/2002 | Garrison et al. |
| 6,454,799 B1 | 9/2002 | Schreck |
| 6,458,153 B1 | 10/2002 | Bailey et al. |
| 6,461,382 B1 | 10/2002 | Cao |
| 6,482,228 B1 | 11/2002 | Norred |
| 6,527,979 B2 | 3/2003 | Constantz et al. |
| 6,540,782 B2 | 4/2003 | Snyders |
| 6,582,462 B1 | 6/2003 | Andersen et al. |
| 6,652,578 B2 | 11/2003 | Bailey et al. |
| 6,663,667 B2 | 12/2003 | Dehdashtian et al. |
| 6,729,356 B1 | 5/2004 | Baker et al. |
| 6,730,118 B2 | 5/2004 | Spenser et al. |
| 6,733,525 B2 | 5/2004 | Yang et al. |
| 6,767,362 B2 | 7/2004 | Schreck |
| 6,773,456 B1 | 8/2004 | Gordon et al. |
| 6,814,754 B2 | 11/2004 | Greenhalgh |
| 6,830,584 B1 | 12/2004 | Seguin |
| 6,846,325 B2 | 1/2005 | Liddicoat |
| 6,878,162 B2 | 4/2005 | Bales et al. |
| 6,893,460 B2 | 5/2005 | Spenser et al. |
| 6,904,909 B2 | 6/2005 | Andreas et al. |
| 6,908,481 B2 | 6/2005 | Cribier |
| 6,911,040 B2 | 6/2005 | Johnson et al. |
| 7,018,406 B2 | 3/2006 | Seguin et al. |
| 7,018,408 B2 | 3/2006 | Bailey et al. |
| 7,101,396 B2 | 9/2006 | Artof et al. |
| 7,147,663 B1 | 12/2006 | Berg et al. |
| 7,175,652 B2 | 2/2007 | Cook et al. |
| 7,192,441 B2 | 3/2007 | Sherry |
| 7,264,632 B2 | 9/2007 | Wright et al. |
| 7,276,078 B2 | 10/2007 | Spenser et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,462,191 B2 | 12/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,655,034 B2 | 2/2010 | Mitchell et al. |
| 7,731,742 B2 | 6/2010 | Schlick et al. |
| 7,780,725 B2 | 8/2010 | Haug et al. |
| 7,785,366 B2 | 8/2010 | Maurer et al. |
| 7,959,672 B2 | 6/2011 | Salahieh et al. |
| 7,993,394 B2 | 8/2011 | Hariton et al. |
| 8,029,556 B2 | 10/2011 | Rowe |
| 8,105,377 B2 | 1/2012 | Liddicoat |
| 8,128,681 B2 | 3/2012 | Shoemaker et al. |
| 8,167,932 B2 | 5/2012 | Bourang et al. |
| 8,425,593 B2 | 4/2013 | Braido et al. |
| 8,430,925 B2 | 4/2013 | Forster et al. |
| 8,449,606 B2 | 5/2013 | Eliasen et al. |
| 8,652,203 B2 | 2/2014 | Quadri et al. |
| 8,721,717 B2 | 5/2014 | Shoemaker et al. |
| 8,795,357 B2 | 8/2014 | Yohanan et al. |
| 8,808,356 B2 | 8/2014 | Braido et al. |
| 8,845,721 B2 | 9/2014 | Braido et al. |
| 8,979,922 B2 | 3/2015 | Jayasinghe et al. |
| 8,992,608 B2 | 3/2015 | Haug et al. |
| 9,220,594 B2 | 12/2015 | Braido et al. |
| 9,241,794 B2 | 1/2016 | Braido et al. |
| 9,289,296 B2 | 3/2016 | Braido et al. |
| 9,326,856 B2 | 5/2016 | Schraut et al. |
| 9,345,571 B1 | 5/2016 | Braido et al. |
| 9,351,828 B2 | 5/2016 | Braido et al. |
| 9,351,831 B2 | 5/2016 | Braido et al. |
| 9,351,832 B2 | 5/2016 | Braido et al. |
| 9,414,911 B2 | 8/2016 | Braido et al. |
| 9,545,307 B2 | 1/2017 | Braido et al. |
| 9,549,815 B2 | 1/2017 | Braido et al. |
| 9,675,451 B2 * | 6/2017 | Garde .................. A61F 2/2409 |
| 2001/0021872 A1 | 9/2001 | Bailey et al. |
| 2001/0027338 A1 | 10/2001 | Greenberg |
| 2001/0039450 A1 | 11/2001 | Pavcnik et al. |
| 2002/0026094 A1 | 2/2002 | Roth |
| 2002/0032481 A1 | 3/2002 | Gabbay |
| 2002/0138135 A1 | 9/2002 | Duerig et al. |
| 2003/0050694 A1 | 3/2003 | Yang et al. |
| 2003/0074058 A1 | 4/2003 | Sherry |
| 2003/0100939 A1 | 5/2003 | Yodfat et al. |
| 2003/0158597 A1 | 8/2003 | Quiachon et al. |
| 2003/0212454 A1 | 11/2003 | Scott et al. |
| 2003/0236567 A1 * | 12/2003 | Elliot ...................... A61F 2/07 |
| | | 623/1.13 |
| 2004/0033364 A1 | 2/2004 | Spiridigliozzi et al. |
| 2004/0082989 A1 | 4/2004 | Cook et al. |
| 2004/0098096 A1 | 5/2004 | Eton |
| 2004/0186563 A1 | 9/2004 | Lobbi |
| 2004/0186565 A1 | 9/2004 | Schreck |
| 2004/0210304 A1 | 10/2004 | Seguin et al. |
| 2004/0260389 A1 | 12/2004 | Case et al. |
| 2005/0043790 A1 | 2/2005 | Seguin |
| 2005/0096736 A1 | 5/2005 | Osse et al. |
| 2005/0137687 A1 | 6/2005 | Salahieh et al. |
| 2005/0203614 A1 | 9/2005 | Forster et al. |
| 2005/0203617 A1 | 9/2005 | Forster et al. |
| 2005/0234546 A1 | 10/2005 | Nugent et al. |
| 2006/0025857 A1 | 2/2006 | Bergheim et al. |
| 2006/0058872 A1 | 3/2006 | Salahieh et al. |
| 2006/0149350 A1 | 7/2006 | Patel et al. |

(56) References Cited

U.S. PATENT DOCUMENTS

| | | | |
|---|---|---|---|
| 2006/0195184 A1* | 8/2006 | Lane | A61F 2/2409 623/2.38 |
| 2007/0005131 A1 | 1/2007 | Taylor | |
| 2007/0010876 A1 | 1/2007 | Salahieh et al. | |
| 2007/0010877 A1 | 1/2007 | Salahieh et al. | |
| 2007/0073387 A1 | 3/2007 | Forster et al. | |
| 2007/0112422 A1 | 5/2007 | Dehdashtian | |
| 2007/0203503 A1 | 8/2007 | Salahieh et al. | |
| 2007/0203575 A1 | 8/2007 | Forster et al. | |
| 2007/0265700 A1 | 11/2007 | Eliasen et al. | |
| 2008/0114442 A1 | 5/2008 | Mitchell et al. | |
| 2008/0125853 A1 | 5/2008 | Bailey et al. | |
| 2008/0154355 A1* | 6/2008 | Benichou | A61F 2/2415 623/1.26 |
| 2009/0099653 A1 | 4/2009 | Suri et al. | |
| 2009/0132035 A1 | 5/2009 | Roth et al. | |
| 2009/0157175 A1 | 6/2009 | Benichou | |
| 2009/0276040 A1 | 11/2009 | Rowe et al. | |
| 2009/0281619 A1 | 11/2009 | Le et al. | |
| 2009/0319037 A1 | 12/2009 | Rowe et al. | |
| 2009/0319038 A1* | 12/2009 | Gurskis | A61F 2/2409 623/2.36 |
| 2010/0049313 A1 | 2/2010 | Alon et al. | |
| 2010/0168839 A1 | 7/2010 | Braido et al. | |
| 2010/0168844 A1 | 7/2010 | Toomes et al. | |
| 2010/0198347 A1 | 8/2010 | Zakay et al. | |
| 2011/0015729 A1 | 1/2011 | Jimenez et al. | |
| 2011/0098802 A1* | 4/2011 | Braido | A61F 2/2412 623/1.26 |
| 2012/0035719 A1 | 2/2012 | Forster et al. | |
| 2012/0089223 A1* | 4/2012 | Nguyen | A61F 2/2418 623/2.14 |
| 2012/0123529 A1* | 5/2012 | Levi | A61F 2/2412 623/2.11 |
| 2012/0215303 A1 | 8/2012 | Quadri et al. | |
| 2012/0259409 A1 | 10/2012 | Nguyen et al. | |
| 2013/0018458 A1* | 1/2013 | Yohanan | A61F 2/2418 623/2.18 |
| 2013/0023985 A1 | 1/2013 | Khairkhahan et al. | |
| 2013/0144382 A1* | 6/2013 | DeStefano | A61F 2/2412 623/2.14 |
| 2013/0190857 A1 | 7/2013 | Mitra et al. | |
| 2013/0274873 A1 | 10/2013 | Delaloye et al. | |
| 2013/0317598 A1 | 11/2013 | Rowe et al. | |
| 2013/0331929 A1* | 12/2013 | Mitra | A61L 31/145 623/2.11 |
| 2013/0338765 A1 | 12/2013 | Braido et al. | |
| 2014/0194981 A1* | 7/2014 | Menk | A61F 2/2418 623/2.17 |
| 2014/0200661 A1 | 7/2014 | Pintor et al. | |
| 2014/0257474 A1* | 9/2014 | Roeder | A61F 2/2412 623/2.17 |
| 2014/0277417 A1* | 9/2014 | Schraut | A61F 2/2403 623/2.17 |
| 2014/0277419 A1 | 9/2014 | Garde et al. | |
| 2014/0277424 A1 | 9/2014 | Oslund | |
| 2014/0277426 A1* | 9/2014 | Dakin | A61F 2/246 623/2.38 |
| 2014/0330372 A1 | 11/2014 | Weston et al. | |
| 2014/0343671 A1 | 11/2014 | Yohanan et al. | |
| 2014/0350663 A1 | 11/2014 | Braido et al. | |
| 2014/0350667 A1 | 11/2014 | Braido et al. | |
| 2015/0073541 A1 | 3/2015 | Salahieh et al. | |
| 2015/0073545 A1 | 3/2015 | Braido | |
| 2015/0073546 A1* | 3/2015 | Braido | A61F 2/2418 623/2.18 |
| 2015/0157455 A1 | 6/2015 | Hoang et al. | |
| 2015/0216657 A1* | 8/2015 | Braido | A61F 2/2418 623/2.17 |
| 2015/0282932 A1 | 10/2015 | Neuman et al. | |
| 2015/0327996 A1* | 11/2015 | Fahim | A61F 2/2418 623/2.17 |
| 2016/0022444 A1* | 1/2016 | Delaloye | A61F 2/2418 623/1.11 |
| 2016/0175096 A1* | 6/2016 | Dienno | A61F 2/2418 623/2.13 |
| 2016/0213466 A1 | 7/2016 | Braido et al. | |
| 2016/0213468 A1 | 7/2016 | Braido et al. | |
| 2016/0235525 A1* | 8/2016 | Rothstein | A61F 2/2418 |
| 2016/0242904 A1 | 8/2016 | Braido et al. | |
| 2016/0317305 A1* | 11/2016 | Pelled | B29C 66/53245 |
| 2016/0338823 A1* | 11/2016 | Akingba | A61F 2/07 |
| 2017/0049566 A1* | 2/2017 | Zeng | A61F 2/2418 |
| 2017/0196687 A1* | 7/2017 | Braido | A61F 2/2418 |
| 2017/0231761 A1* | 8/2017 | Cohen-Tzemach | A61F 2/2418 623/2.18 |
| 2017/0281193 A1* | 10/2017 | Asiryatham | A61B 17/12122 |
| 2017/0312075 A1* | 11/2017 | Fahim | A61F 2/2412 |

FOREIGN PATENT DOCUMENTS

| | | |
|---|---|---|
| DE | 19546692 A1 | 6/1997 |
| DE | 19857887 A1 | 7/2000 |
| DE | 19907646 A1 | 8/2000 |
| EP | 0103546 A1 | 3/1984 |
| EP | 0592410 A1 | 4/1994 |
| EP | 0597967 A1 | 5/1994 |
| EP | 0850607 A1 | 7/1998 |
| EP | 1796597 A2 | 6/2007 |
| EP | 2155114 A1 | 2/2010 |
| EP | 2299938 A2 | 3/2011 |
| EP | 2572676 A3 | 8/2013 |
| EP | 2572675 A3 | 9/2013 |
| EP | 2698129 A1 | 2/2014 |
| EP | 2745805 B1 | 6/2015 |
| EP | 2749254 B1 | 6/2015 |
| EP | 2967851 A2 | 1/2016 |
| EP | 2926766 B1 | 2/2016 |
| EP | 2815725 B1 | 4/2016 |
| EP | 2815724 B1 | 6/2016 |
| EP | 3028670 A1 | 6/2016 |
| EP | 3028671 A1 | 6/2016 |
| EP | 2815723 B1 | 7/2016 |
| EP | 3025680 B1 | 2/2017 |
| EP | 3025681 B1 | 2/2017 |
| EP | 2190385 B1 | 3/2017 |
| FR | 2788217 A1 | 7/2000 |
| FR | 2815844 A1 | 5/2002 |
| SU | 1271508 A1 | 11/1986 |
| WO | 1991017720 A1 | 11/1991 |
| WO | 1993001768 A1 | 2/1993 |
| WO | 1998029057 A1 | 7/1998 |
| WO | 1997048350 A8 | 6/1999 |
| WO | 1999040964 A1 | 8/1999 |
| WO | 1999047075 A1 | 9/1999 |
| WO | 00/41652 A1 | 7/2000 |
| WO | 00/44313 A1 | 8/2000 |
| WO | 00/47139 A1 | 8/2000 |
| WO | 0044313 A8 | 11/2000 |
| WO | 0106959 A1 | 2/2001 |
| WO | 01/49213 A2 | 7/2001 |
| WO | 01/54625 A1 | 8/2001 |
| WO | 01/62189 A1 | 8/2001 |
| WO | 01/64137 A1 | 9/2001 |
| WO | 01/76510 A2 | 10/2001 |
| WO | 02/22054 A1 | 3/2002 |
| WO | 0219951 A1 | 3/2002 |
| WO | 02/36048 A1 | 5/2002 |
| WO | 02/47575 A2 | 6/2002 |
| WO | 03/047468 A1 | 6/2003 |
| WO | 03037222 A3 | 10/2003 |
| WO | 03088873 A1 | 10/2003 |
| WO | 03/096932 A1 | 11/2003 |
| WO | 03003949 A3 | 1/2004 |
| WO | 2005034812 A1 | 4/2005 |
| WO | 2005084595 A1 | 9/2005 |
| WO | 2005102015 A2 | 11/2005 |
| WO | 2006005015 A3 | 4/2006 |
| WO | 2006111391 A1 | 10/2006 |
| WO | 2006/138173 A2 | 12/2006 |
| WO | 2007047488 A2 | 4/2007 |

(56) References Cited

FOREIGN PATENT DOCUMENTS

| WO | 2007067942 A1 | 6/2007 |
|---|---|---|
| WO | 2007097983 A2 | 8/2007 |
| WO | 08/005405 A2 | 1/2008 |
| WO | 2008015257 A2 | 2/2008 |
| WO | 08/091515 A2 | 7/2008 |
| WO | 09/033469 A1 | 3/2009 |
| WO | 2010121076 A2 | 10/2010 |

OTHER PUBLICATIONS

H.R. Andersen "History of Percutaneous Aortic Valve Prosthesis," Herz No. 34. pp. 343-346. 2009.
Pavcnik, et al. "Development and initial Experimental Evaluation of a Prosthetic Aortic Valve for Transcatheter Placement," Cardiovascular Radiology, vol. 183, No. 1. pp. 151-154. 1992.
Bailey, S. "Percutaneous Expandable Prosthetic Valves," Textbook of Interventional Cardiology vol. 2, 2nd Ed. pp. 1268-1276. 1994.
Al-Khaja, et al. "Eleven Years' Experience with Carpentier-Edwards Biological Valves in Relation to Survival and Complications," European Journal of Cardiothoracic Surgery, vol. 3. pp. 305-311. 1989.
Ross, "Aortic Valve Surgery," At a meeting of the Council on Aug. 4, 1966. pp. 192-197.
Sabbah, et al. "Mechanical Factors in the Degeneration of Porcine Bioprosthetic Valves: An Overview," Journal of Cardiac Surgery, vol. 4, No. 4. pp. 302-309. 1989.
Wheatley, "Valve Prostheses," Operative Surgery, 4th ed. pp. 415-424. 1986.
Uchida, "Modifications of Gianturco Expandable Wire Stents," American Journal of Roentgenology, vol. 150. pp. 1185-1187. 1986.

* cited by examiner

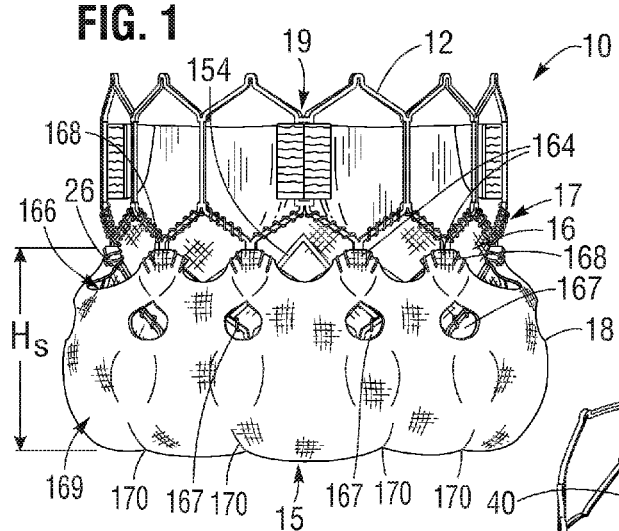
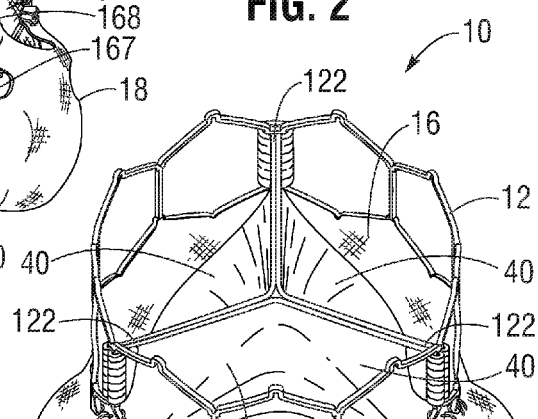
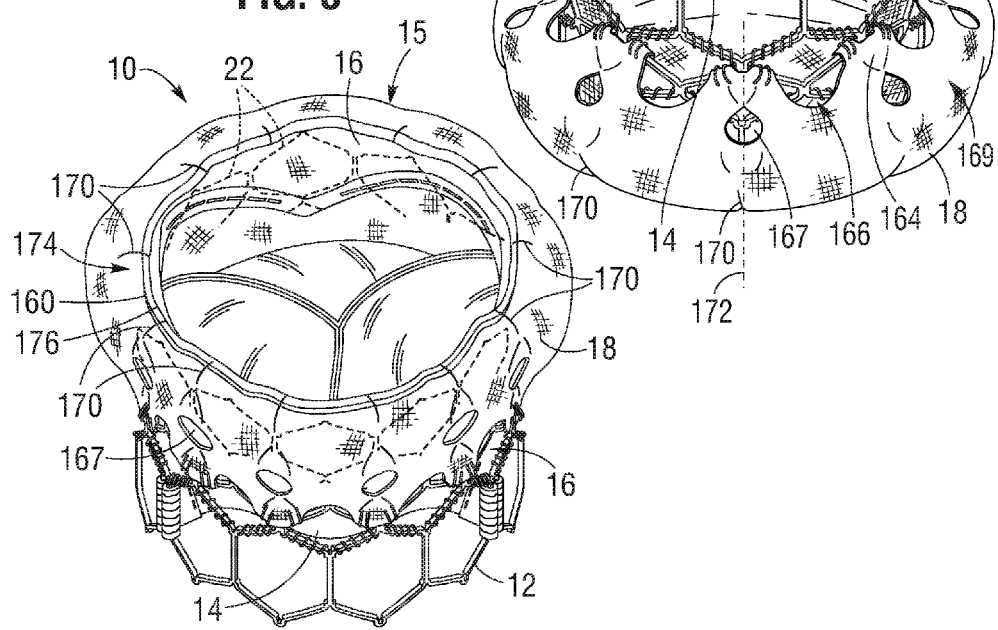

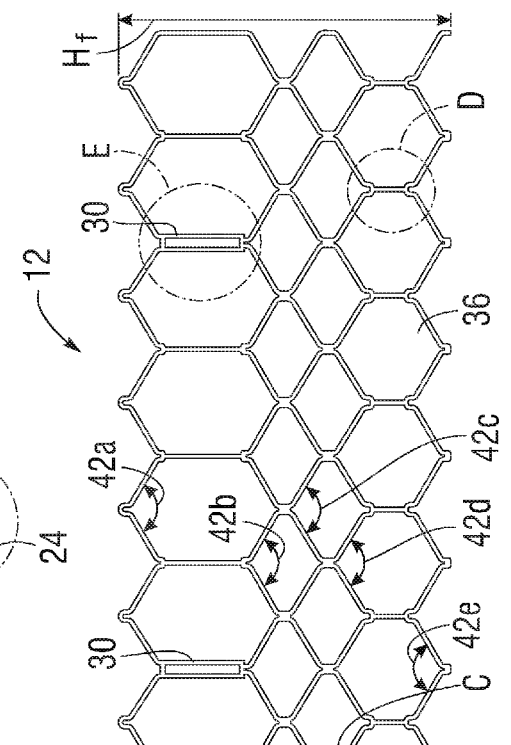
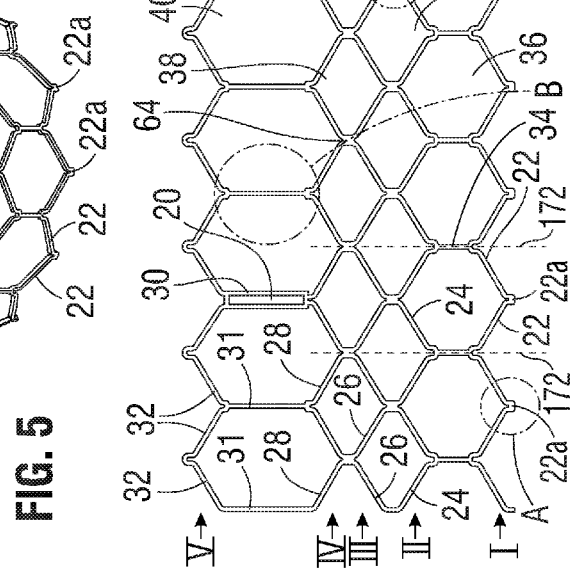

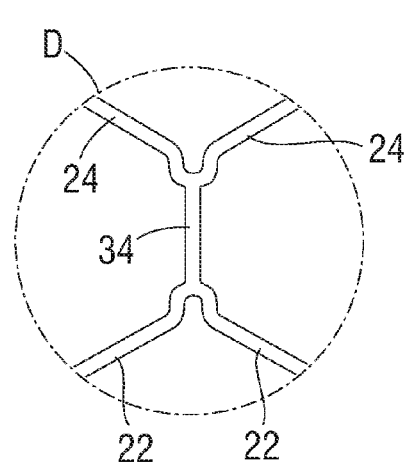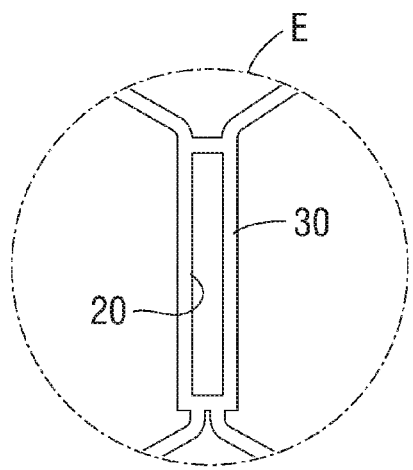

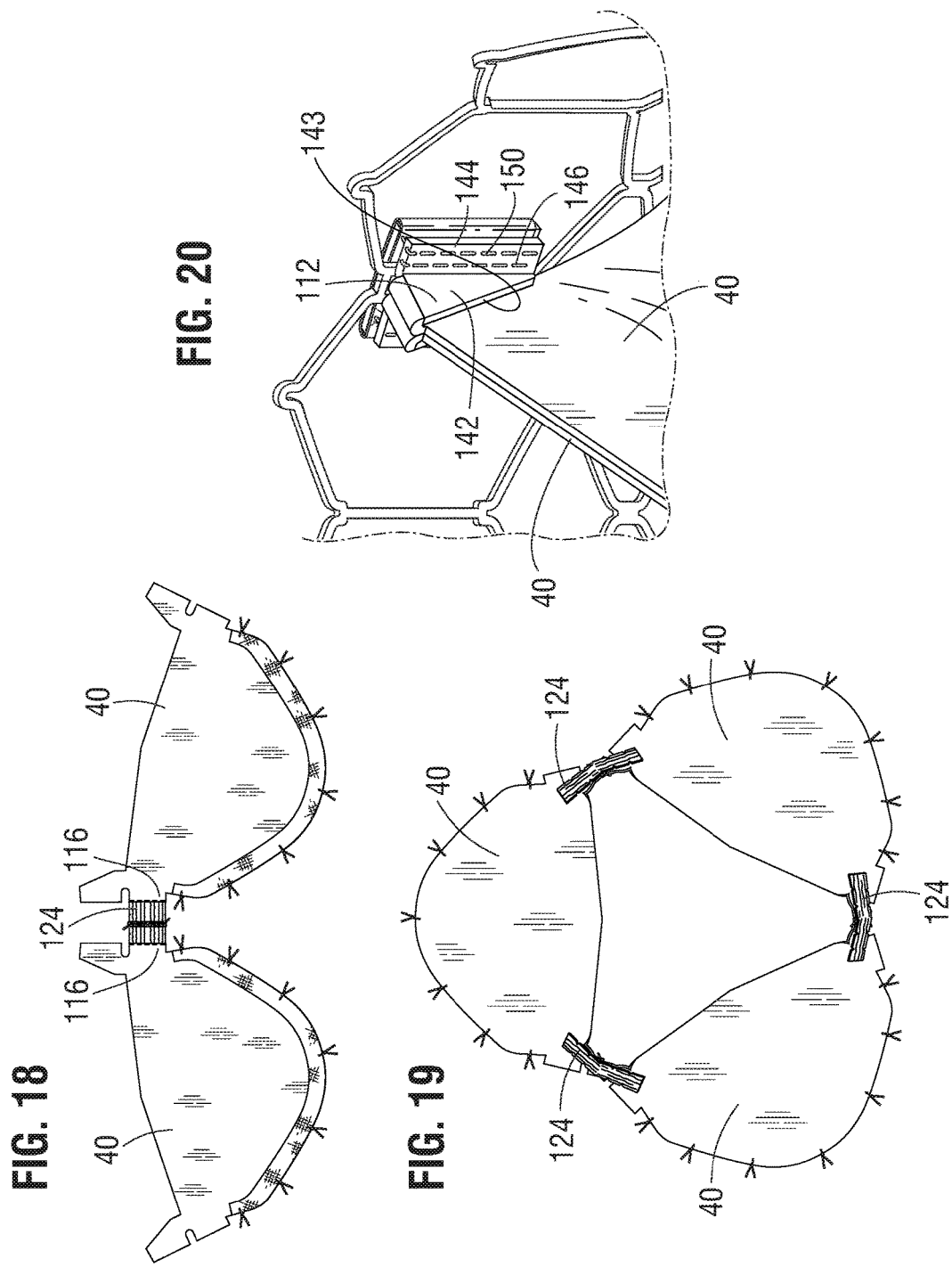

PROSTHETIC HEART VALVE

CROSS REFERENCE TO RELATED APPLICATIONS

This application claims the benefit of U.S. Provisional Application No. 62/192,515, filed on Jul. 14, 2015, which application is incorporated by reference herein.

FIELD

The present disclosure relates to implantable, expandable prosthetic devices and to methods and apparatuses for such prosthetic devices.

BACKGROUND

The human heart can suffer from various valvular diseases. These valvular diseases can result in significant malfunctioning of the heart and ultimately require replacement of the native valve with an artificial valve. There are a number of known artificial valves and a number of known methods of implanting these artificial valves in humans. Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For example, collapsible transcatheter prosthetic heart valves can be crimped to a compressed state and percutaneously introduced in the compressed state on a catheter and expanded to a functional size at the desired position by balloon inflation or by utilization of a self-expanding frame or stent.

A prosthetic valve for use in such a procedure can include a radially collapsible and expandable frame to which leaflets of the prosthetic valve can be coupled. For example, U.S. Pat. Nos. 6,730,118, 7,393,360, 7,510,575, and 7,993,394, which are incorporated herein by reference, describe exemplary collapsible transcatheter prosthetic heart valves.

A prosthetic valve for use in such a procedure can include a radially collapsible and expandable frame to which leaflets of the prosthetic valve can be coupled, and which can be percutaneously introduced in a collapsed configuration on a catheter and expanded in the desired position by balloon inflation or by utilization of a self-expanding frame or stent. A challenge in catheter-implanted prosthetic valves is control of perivalvular leakage around the valve, which can occur for a period of time following initial implantation. An additional challenge includes the process of crimping such a prosthetic valve to a profile suitable for percutaneous delivery to a subject.

SUMMARY

Embodiments of a radially collapsible and expandable prosthetic valve are disclosed herein that include an improved outer skirt for reducing perivalvular leakage, as well as related methods and apparatuses including such prosthetic valves. In several embodiments, the disclosed prosthetic valves are configured as replacement heart valves for implantation into a subject.

In one representative embodiment, an implantable prosthetic valve can comprise an annular frame comprising an inflow end and an outflow end and being radially collapsible and expandable between a radially collapsed configuration and a radially expanded configuration, the frame defining an axial direction extending from the inflow end to the outflow end, a leaflet structure positioned within the frame and secured thereto, and an annular outer skirt positioned around an outer surface of the frame, wherein the outer skirt comprises an inflow edge secured to the frame at a first location, an outflow edge comprising a plurality of alternating projections and notches, wherein the projections are secured to the frame at a second location, and the notches are not directly secured to the frame, an intermediate portion between the inflow edge and the outflow edge that comprises a plurality of openings.

In some embodiments, when the frame is in the collapsed configuration, the axial distance between the inflow edge of the outer skirt and the outflow edge of the outer skirt can be greater than when the valve is in the expanded configuration, increasing tension of the intermediate portion of the outer skirt.

In some embodiments, the outer skirt can comprise a first height, and the frame in the radially expanded configuration can comprise a second height, and wherein a ratio of the first height to the second height can be about 0.75 to about 0.95. In some embodiments, the ratio of the first height to the second height can be about 0.86.

In some embodiments, the outer skirt can comprise a plurality of axially extending creases. In some embodiments, the creases are formed by suturing and/or ultrasonic welding portions of the outer skirt to each other.

In some embodiments, each of the openings of the outer skirt can be circumferentially aligned with a respective crease of the outer skirt. In some embodiments, each of the creases of the outer skirt can be circumferentially aligned with a respective projection of the outer skirt.

In some embodiments, the outer skirt can be positioned relative to the frame such that each of the creases of the outer skirt is circumferentially positioned between a respective pair of apices formed by struts at the inflow end of the frame. In some embodiments, each of the creases can be positioned equidistantly between a respective pair of apices.

In some embodiments, the prosthetic valve can further comprise an annular inner skirt positioned around an inner surface of the frame, wherein the inner skirt can comprise an inflow edge secured to the frame at a third location, an outflow edge secured to the frame at a fourth location. In some of those embodiments, the inflow edge of the outer skirt can be attached to the inflow edge of the inner skirt. In such embodiments, the inflow edge of the outer skirt can be attached to the inflow edge of the inner skirt with ultrasonic welding.

In some embodiments, at least a portion of the outer skirt can be configured to retract radially within the frame when the frame is the radially collapsed configuration. In some embodiments, the outer skirt can be configured such that blood can flow through the openings and the notches of the outer skirt and blood can flow through a space between the outer skirt and the frame. In some embodiments, the outer skirt is attached to the frame such that each of the projections of the outer skirt is circumferentially positioned between a respective pair of apices formed by struts at the inflow end of the frame.

In another representative embodiment, an assembly for implanting a prosthetic heart valve in a patient's body is provided. The assembly can comprise a delivery apparatus comprising an elongate shaft, and a prosthetic heart valve mounted on the shaft in a radially collapsed configuration for delivery into the body.

In another representative embodiment, a method of manufacturing a prosthetic valve is provided. The method can comprise forming at least one permanent crease in an annular outer skirt of the prosthetic valve, and securing the outer skirt to an annular frame of the prosthetic valve. In some embodiments, forming the at least one crease comprises suturing and/or ultrasonic welding portions of the outer skirt to each other.

In some embodiments, the method can further comprise forming at least one opening in the outer skirt, wherein the at least one opening is circumferentially aligned with a respective at least one crease. In some embodiments, the method can further comprise positioning the outer skirt relative to an annular frame such that the at least one crease is circumferentially disposed between struts of the frame.

In another representative embodiment, an implantable prosthetic valve can comprise an annular frame comprising an inflow end and an outflow end and being radially collapsible and expandable between a radially collapsed configuration and a radially expanded configuration, the frame defining an axial direction extending from the inflow end to the outflow end, a leaflet structure positioned within the frame and secured thereto, and an annular outer skirt positioned around an outer surface of the frame, wherein the outer skirt comprises an inflow edge secured to the frame at a first location, an outflow edge secured to the frame at a second location, a plurality of axially extending creases, wherein the creases are configured to cause at least a portion of the outer skirt to retract radially within the frame when the frame is radially collapsed from the expanded configuration.

In some embodiments, the outer skirt can further comprise an intermediate portion between the inflow edge and the outflow edge that comprises a plurality of openings.

The foregoing and other features and advantages of this disclosure will become more apparent from the following detailed description of several embodiments which proceeds with reference to the accompanying figures.

BRIEF DESCRIPTION OF THE DRAWINGS

FIGS. 1-3 show an exemplary embodiment of a prosthetic heart valve.

FIGS. 4-10 show an exemplary frame of the prosthetic heart valve of FIG. 1.

FIGS. 18-19 show the assembly of an exemplary leaflet structure.

FIG. 20 shows the assembly of commissure portions of the leaflet structure with window frame portions of the frame.

DETAILED DESCRIPTION

Figure 11:
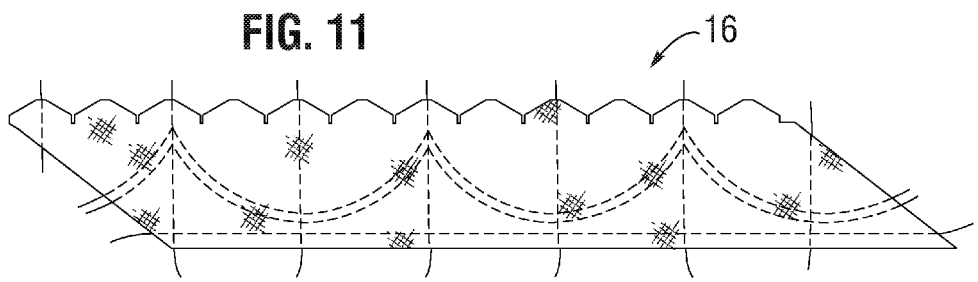
FIGS. 11-12 show an exemplary inner skirt of the prosthetic heart valve of FIG. 1.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B", "C", "A and B", "A and C", "B and C", or "A, B, and C".

As used herein, the term "coupled" generally means physically coupled or linked and does not exclude the presence of intermediate elements between the coupled items absent specific contrary language.

FIGS. 1-3 show various views of a prosthetic heart valve 10, according to one embodiment. The illustrated prosthetic valve is adapted to be implanted in the native aortic annulus, although in other embodiments it can be adapted to be implanted in the other native annuluses of the heart (e.g., the pulmonary, mitral, and tricuspid valves). The prosthetic valve can also be adapted to be implanted in other tubular organs or passageways in the body. The prosthetic valve 10 can have four main components: a stent or frame 12, a valvular structure 14, an inner skirt 16, and a perivalvular sealing means or sealing member. The prosthetic valve 10 can have an inflow end portion 15, an intermediate portion 17, and an outflow end portion 19. In the illustrated embodiment, the perivalvular sealing means comprises an outer skirt 18.

The valvular structure 14 can comprise three leaflets 40, collectively forming a leaflet structure, which can be arranged to collapse in a tricuspid arrangement, as best shown in FIG. 2. The lower edge of leaflet structure 14 desirably has an undulating, curved scalloped shape (suture line 154 shown in FIG. 22 tracks the scalloped shape of the leaflet structure). By forming the leaflets with this scalloped geometry, stresses on the leaflets are reduced, which in turn improves durability of the prosthetic valve. Moreover, by virtue of the scalloped shape, folds and ripples at the belly of each leaflet (the central region of each leaflet), which can cause early calcification in those areas, can be eliminated or at least minimized. The scalloped geometry also reduces the amount of tissue material used to form leaflet structure, thereby allowing a smaller, more even crimped profile at the inflow end of the prosthetic valve. The leaflets 40 can be formed of pericardial tissue (e.g., bovine pericardial tissue), biocompatible synthetic materials, or various other suitable natural or synthetic materials as known in the art and described in U.S. Pat. No. 6,730,118, which is incorporated by reference herein.

The bare frame 12 is shown in FIG. 4. The frame 12 can be formed with a plurality of circumferentially spaced slots, or commissure windows, 20 (three in the illustrated embodiment) that are adapted to mount the commissures of the valvular structure 14 to the frame, as described in greater detail below. The frame 12 can be made of any of various suitable plastically-expandable materials (e.g., stainless steel, etc.) or self-expanding materials (e.g., nickel titanium alloy (NiTi), such as nitinol) as known in the art. When constructed of a plastically-expandable material, the frame 12 (and thus the prosthetic valve 10) can be crimped to a radially collapsed configuration on a delivery catheter and then expanded inside a patient by an inflatable balloon or equivalent expansion mechanism. When constructed of a self-expandable material, the frame 12 (and thus the prosthetic valve 10) can be crimped to a radially collapsed configuration and restrained in the collapsed configuration by insertion into a sheath or equivalent mechanism of a delivery catheter. Once inside the body, the prosthetic valve can be advanced from the delivery sheath, which allows the prosthetic valve to expand to its functional size.

Suitable plastically-expandable materials that can be used to form the frame 12 include, without limitation, stainless steel, a biocompatible, high-strength alloys (e.g., a cobalt-chromium or a nickel-cobalt-chromium alloys), polymers, or combinations thereof. In particular embodiments, frame 12 is made of a nickel-cobalt-chromium-molybdenum alloy, such as MP35N® alloy (SPS Technologies, Jenkintown, Pa.), which is equivalent to UNS R30035 alloy (covered by ASTM F562-02). MP35N® alloy/UNS R30035 alloy comprises 35% nickel, 35% cobalt, 20% chromium, and 10% molybdenum, by weight. It has been found that the use of MP35N® alloy to form frame 12 provides superior structural results over stainless steel. In particular, when MP35N® alloy is used as the frame material, less material is needed to achieve the same or better performance in radial and crush force resistance, fatigue resistances, and corrosion resistance. Moreover, since less material is required, the crimped profile of the frame can be reduced, thereby providing a lower profile prosthetic valve assembly for percutaneous delivery to the treatment location in the body.

Referring to FIGS. 4 and 5, the frame 12 in the illustrated embodiment comprises a first, lower row I of angled struts 22 arranged end-to-end and extending circumferentially at the inflow end of the frame; a second row II of circumferentially extending, angled struts 24; a third row III of circumferentially extending, angled struts 26; a fourth row IV of circumferentially extending, angled struts 28; and a fifth row V of circumferentially extending, angled struts 32 at the outflow end of the frame. A plurality of substantially straight axially extending struts 34 can be used to interconnect the struts 22 of the first row I with the struts 24 of the second row II. The fifth row V of angled struts 32 are connected to the fourth row IV of angled struts 28 by a plurality of axially extending window frame portions 30 (which define the commissure windows 20) and a plurality of axially extending struts 31. Each axial strut 31 and each frame portion 30 extends from a location defined by the convergence of the lower ends of two angled struts 32 to another location defined by the convergence of the upper ends of two angled struts 28. FIGS. 6, 7, 8, 9, and 10 are enlarged views of the portions of the frame 12 identified by letters A, B, C, D, and E, respectively, in FIG. 5.

Each commissure window frame portion 30 mounts a respective commissure of the leaflet structure 14. As can be seen each frame portion 30 is secured at its upper and lower ends to the adjacent rows of struts to provide a robust configuration that enhances fatigue resistance under cyclic loading of the prosthetic valve compared to known, cantilevered struts for supporting the commissures of the leaflet structure. This configuration enables a reduction in the frame wall thickness to achieve a smaller crimped diameter of the prosthetic valve. In particular embodiments, the thickness T of the frame 12 (FIG. 4) measured between the inner diameter and outer diameter is about 0.48 mm or less.

The struts and frame portions of the frame collectively define a plurality of open cells of the frame. At the inflow end of the frame 12, struts 22, struts 24, and struts 34 define a lower row of cells defining openings 36. The second, third, and fourth rows of struts 24, 26, and 28 define two intermediate rows of cells defining openings 38. The fourth and fifth rows of struts 28 and 32, along with frame portions 30 and struts 31, define an upper row of cells defining openings 40. The openings 40 are relatively large and are sized to allow portions of the leaflet structure 14 to protrude, or bulge, into and/or through the openings 40 when the frame 12 is crimped in order to minimize the crimping profile.

Figure 14:
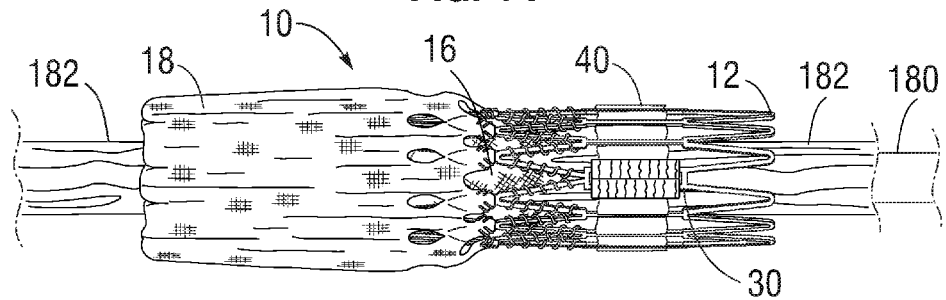
FIG. 14 shows the prosthetic heart valve of FIG. 1 in a collapsed configuration and mounted on an exemplary balloon catheter.

As best shown in FIG. 7, the lower end of the strut 31 is connected to two struts 28 at a node or junction 44, and the upper end of the strut 31 is connected to two struts 32 at a node or junction 46. The strut 31 can have a thickness S1 that is less than the thicknesses S2 of the junctions 44, 46. The junctions 44, 46, along with junctions 64, prevent full closure of openings 40. FIG. 14 shows the prosthetic valve 10 crimped on a balloon catheter. As can be seen, the geometry of the struts 31, and junctions 44, 46, and 64 assists in creating enough space in openings 40 in the collapsed configuration to allow portions of the prosthetic leaflets to protrude or bulge outwardly through openings. This allows the prosthetic valve to be crimped to a relatively smaller diameter than if all of the leaflet material were constrained within the crimped frame.

The frame 12 is configured to reduce, to prevent, or to minimize possible over-expansion of the prosthetic valve at a predetermined balloon pressure, especially at the outflow end portion 19 of the frame, which supports the leaflet structure 14. In one aspect, the frame is configured to have relatively larger angles 42a, 42b, 42c, 42d, 42e between struts, as shown in FIG. 5. The larger the angle, the greater the force required to open (expand) the frame. As such, the angles between the struts of the frame can be selected to limit radial expansion of the frame at a given opening pressure (e.g., inflation pressure of the balloon). In particular embodiments, these angles are at least 110 degrees or greater when the frame is expanded to its functional size, and even more particularly these angles are up to about 120 degrees when the frame is expanded to its functional size.

In addition, the inflow and outflow ends of a frame generally tend to over-expand more so than the middle portion of the frame due to the "dog-boning" effect of the balloon used to expand the prosthetic valve. To protect against over-expansion of the leaflet structure 14, the leaflet structure desirably is secured to the frame 12 below the upper row of struts 32, as best shown in FIG. 1. Thus, in the event that the outflow end of the frame is over-expanded, the leaflet structure is positioned at a level below where over-expansion is likely to occur, thereby protecting the leaflet structure from over-expansion.

In a known prosthetic valve construction, portions of the leaflets can protrude longitudinally beyond the outflow end of the frame when the prosthetic valve is crimped if the leaflets are mounted too close to the distal end of the frame. If the delivery catheter on which the crimped prosthetic valve is mounted includes a pushing mechanism or stop member that pushes against or abuts the outflow end of the prosthetic valve (for example, to maintain the position of the crimped prosthetic valve on the delivery catheter), the pushing member or stop member can damage the portions of the exposed leaflets that extend beyond the outflow end of the frame. Another benefit of mounting the leaflets at a location spaced away from the outflow end of the frame is that when the prosthetic valve is crimped on a delivery catheter, the outflow end of the frame 12 rather than the leaflets 40 is the proximal-most component of the prosthetic valve 10. As such, if the delivery catheter includes a pushing mechanism or stop member that pushes against or abuts the outflow end of the prosthetic valve, the pushing mechanism or stop member contacts the outflow end of the frame, and not leaflets 40, so as to avoid damage to the leaflets.

Also, as can be seen in FIG. 5, the openings 36 of the lowermost row of openings in the frame are relatively larger than the openings 38 of the two intermediate rows of openings. This allows the frame, when crimped, to assume an overall tapered shape that tapers from a maximum diameter at the outflow end of the prosthetic valve to a minimum diameter at the inflow end of the prosthetic valve. When crimped, the frame 12 has a reduced diameter region extending along a portion of the frame adjacent the inflow end of the frame that generally corresponds to the region of the frame covered by the outer skirt 18. In some embodiments, the reduced diameter region is reduced compared to the diameter of the upper portion of the frame (which is not covered by the outer skirt) such that the outer skirt 18 does not increase the overall crimp profile of the prosthetic valve. When the prosthetic valve is deployed, the frame can expand to the generally cylindrical shape shown in FIG. 4. In one example, the frame of a 26-mm prosthetic valve, when crimped, had a first diameter of 14 French at the outflow end of the prosthetic valve and a second diameter of 12 French at the inflow end of the prosthetic valve.

The main functions of the inner skirt 16 are to assist in securing the valvular structure 14 to the frame 12 and to assist in forming a good seal between the prosthetic valve and the native annulus by blocking the flow of blood through the open cells of the frame 12 below the lower edge of the leaflets. The inner skirt 16 desirably comprises a tough, tear resistant material such as polyethylene terephthalate (PET), although various other synthetic materials or natural materials (e.g., pericardial tissue) can be used. The thickness of the skirt desirably is less than about 0.15 mm (about 6 mil), and desirably less than about 0.1 mm (about 4 mil), and even more desirably about 0.05 mm (about 2 mil). In particular embodiments, the skirt 16 can have a variable thickness, for example, the skirt can be thicker at least one of its edges than at its center. In one implementation, the skirt 16 can comprise a PET skirt having a thickness of about 0.07 mm at its edges and about 0.06 mm at its center. The thinner skirt can provide for better crimping performances while still providing good perivalvular sealing.

Figure 21:
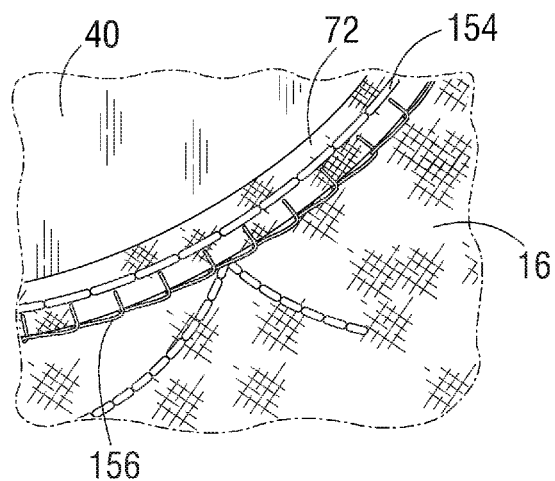
FIGS. 21-22 show the assembly of the leaflet structure with the inner skirt along a lower edge of the leaflets.
Figure 22:
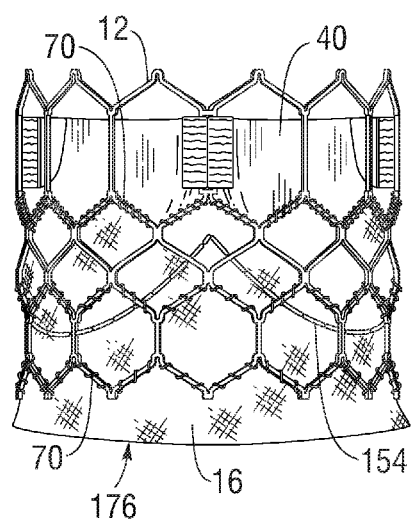

The skirt 16 can be secured to the inside of frame 12 via sutures 70, as shown in FIG. 22. Valvular structure 14 can be attached to the skirt via one or more reinforcing strips 72 (which collectively can form a sleeve), for example thin, PET reinforcing strips, discussed below, which enables a secure suturing and protects the pericardial tissue of the leaflet structure from tears. Valvular structure 14 can be sandwiched between skirt 16 and the thin PET strips 72 as shown in FIG. 21. Sutures 154, which secure the PET strip and the leaflet structure 14 to skirt 16, can be any suitable suture, such as Ethibond Excel® PET suture (Johnson & Johnson, New Brunswick, N.J.). Sutures 154 desirably track the curvature of the bottom edge of leaflet structure 14, as described in more detail below.

Known fabric skirts may comprise a weave of warp and weft fibers that extend perpendicularly to each other and with one set of the fibers extending longitudinally between the upper and lower edges of the skirt. When the metal frame to which the fabric skirt is secured is radially compressed, the overall axial length of the frame increases. Unfortunately, a fabric skirt with limited elasticity cannot elongate along with the frame and therefore tends to deform the struts of the frame and to prevent uniform crimping.

Figure 12:
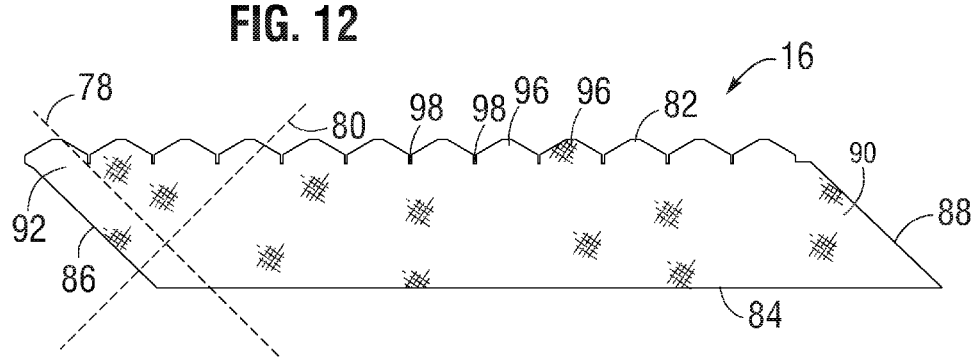

Referring to FIG. 12, in contrast to known fabric skirts, the skirt 16 desirably is woven from a first set of fibers, or yarns or strands, 78 and a second set of fibers, or yarns or strands, 80, both of which are non-perpendicular to the upper edge 82 and the lower edge 84 of the skirt. In particular embodiments, the first set of fibers 78 and the second set of fibers 80 extend at angles of about 45 degrees (e.g., 15-75 degrees or 30-60 degrees) relative to the upper and lower edges 82, 84. For example, the skirt 16 can be formed by weaving the fibers at 45 degree angles relative to the upper and lower edges of the fabric. Alternatively, the skirt can be diagonally cut (cut on a bias) from a vertically woven fabric (where the fibers extend perpendicularly to the edges of the material) such that the fibers extend at 45 degree angles relative to the cut upper and lower edges of the skirt. As further shown in FIG. 12, the opposing short edges 86, 88 of the skirt desirably are non-perpendicular to the upper and lower edges 82, 84. For example, the short edges 86, 88 desirably extend at angles of about 45 degrees relative to the upper and lower edges and therefore are aligned with the first set of fibers 78. Therefore the overall general shape of the skirt is that of a rhomboid or parallelogram.

Figure 13:
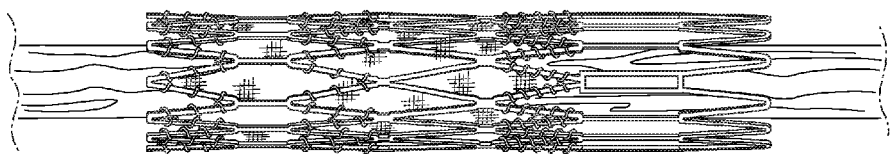
FIG. 13 shows another embodiment of a prosthetic heart valve with a deformed frame.

FIG. 13 shows an example of a crimped prosthetic valve with a skirt having fibers that extend perpendicular to and/or longitudinally between the upper and lower edges of the skirt. During crimping, this fiber orientation can cause the struts to deform non-uniformly. Moreover, when crimped, the fabric tends to bunch or create bulges of excess material in certain locations, which limits the minimum crimping profile and prevents uniform crimping.

Figure 15:
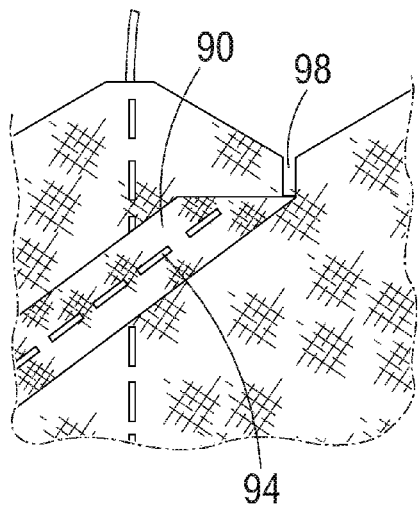
FIGS. 15-17 show the assembly of the inner skirt of FIG. 11 with the frame of FIG. 4.
Figure 16:
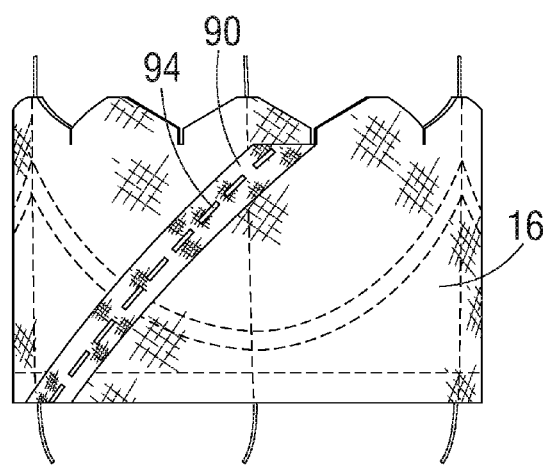
Figure 17:
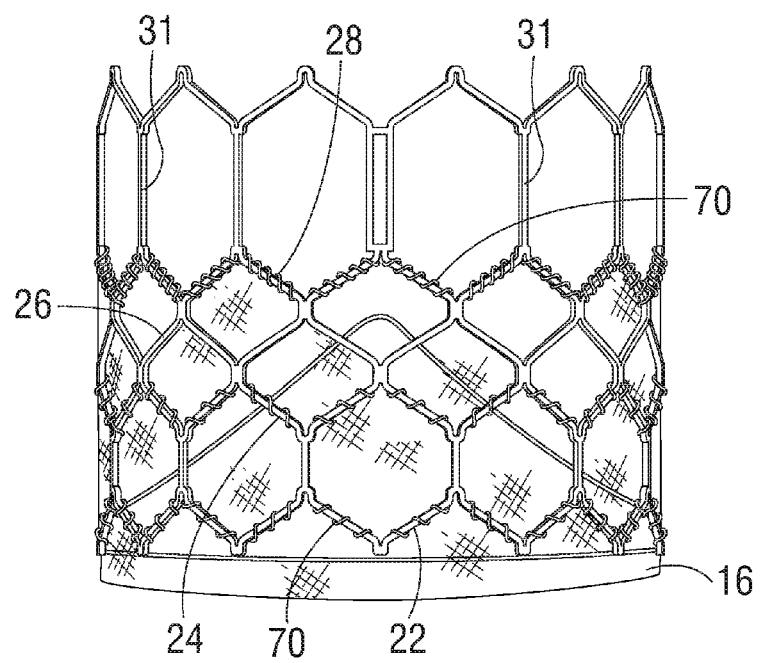

FIGS. 15 and 16 show the inner skirt 16 after opposing short edge portions 90, 92 have been sewn together to form the annular shape of the skirt. As shown, the edge portion 90 can be placed in an overlapping relationship relative to the opposite edge portion 92, and the two edge portions can be sewn together with a diagonally extending suture line 94 that is parallel to short edges 86, 88. The upper edge portion of the inner skirt 16 can be formed with a plurality of projections 96 that define an undulating shape that generally follows the shape or contour of the fourth row of struts 28 immediately adjacent the lower ends of axial struts 31. In this manner, as best shown in FIG. 17, the upper edge of the inner skirt 16 can be tightly secured to struts 28 with sutures 70. The inner skirt 16 can also be formed with slits 98 to facilitate attachment of the skirt to the frame. Slits 98 are dimensioned so as to allow an upper edge portion of the inner skirt 16 to be partially wrapped around struts 28 and to reduce stresses in the skirt during the attachment procedure. For example, in the illustrated embodiment, the inner skirt 16 is placed on the inside of frame 12 and an upper edge portion of the skirt is wrapped around the upper surfaces of struts 28 and secured in place with sutures 70. Wrapping the upper edge portion of the inner skirt 16 around struts 28 in this manner provides for a stronger and more durable attachment of the skirt to the frame. The inner skirt 16 can also be secured to the first, second, and/or third rows of struts 22, 24, and 26, respectively, with sutures 70.

Referring again to FIG. 12, due to the angled orientation of the fibers relative to the upper and lower edges, the skirt can undergo greater elongation in the axial direction (i.e., in a direction from the upper edge 82 to the lower edge 84).

Thus, when the metal frame 12 is crimped (as shown in FIG. 14), the inner skirt 16 can elongate in the axial direction along with the frame and therefore provide a more uniform and predictable crimping profile. Each cell of the metal frame in the illustrated embodiment includes at least four angled struts that rotate towards the axial direction on crimping (e.g., the angled struts become more aligned with the length of the frame). The angled struts of each cell function as a mechanism for rotating the fibers of the skirt in the same direction of the struts, allowing the skirt to elongate along the length of the struts. This allows for greater elongation of the skirt and avoids undesirable deformation of the struts when the prosthetic valve is crimped.

In addition, the spacing between the woven fibers or yarns can be increased to facilitate elongation of the skirt in the axial direction. For example, for a PET inner skirt 16 formed from 20-denier yarn, the yarn density can be about 15% to about 30% lower than in a typical PET skirt. In some examples, the yarn spacing of the inner skirt 16 can be from about 60 yarns per cm (about 155 yarns per inch) to about 70 yarns per cm (about 180 yarns per inch), such as about 63 yarns per cm (about 160 yarns per inch), whereas in a typical PET skirt the yarn spacing can be from about 85 yarns per cm (about 217 yarns per inch) to about 97 yarns per cm (about 247 yarns per inch). The oblique edges 86, 88 promote a uniform and even distribution of the fabric material along inner circumference of the frame during crimping so as to reduce or minimize bunching of the fabric to facilitate uniform crimping to the smallest possible diameter. Additionally, cutting diagonal sutures in a vertical manner may leave loose fringes along the cut edges. The oblique edges 86, 88 help minimize this from occurring. As noted above, FIG. 13 shows a crimped prosthetic valve with a typical skirt that has fibers that run perpendicularly to the upper and lower edges of the skirt. Compared to the construction of a typical skirt (e.g., FIG. 13), the construction of the inner skirt 16 (e.g., FIG. 14) avoids undesirable deformation of the frame struts and provides more uniform crimping of the frame.

In alternative embodiments, the skirt can be formed from woven elastic fibers that can stretch in the axial direction during crimping of the prosthetic valve. The warp and weft fibers can run perpendicularly and parallel to the upper and lower edges of the skirt, or alternatively, they can extend at angles between 0 and 90 degrees relative to the upper and lower edges of the skirt, as described above.

The inner skirt 16 can be sutured to the frame 12 at locations away from the suture line 154 so that the skirt can be more pliable in that area. This configuration can avoid stress concentrations at the suture line 154, which attaches the lower edges of the leaflets to the inner skirt 16.

As noted above, the leaflet structure 14 in the illustrated embodiment includes three flexible leaflets 40 (although a greater or a smaller number of leaflets can be used). Additional information regarding the leaflets, as well as additional information regarding skirt material, can be found, for example, in U.S. patent application Ser. No. 14/704,861, filed May 5, 2015, which is incorporated by reference in its entirety.

The leaflets 40 can be secured to one another at their adjacent sides to form commissures 122 of the leaflet structure. A plurality of flexible connectors 124 (one of which is shown in FIG. 18) can be used to interconnect pairs of adjacent sides of the leaflets and to mount the leaflets to the commissure window frame portions 30 (FIG. 5).

FIG. 18 shows the adjacent sides of two leaflets 40 interconnected by a flexible connector 124. Three leaflets 40 can be secured to each other side-to-side using three flexible connectors 124, as shown in FIG. 19. Additional information regarding connecting the leaflets to each other, as well as connecting the leaflets to the frame, can be found, for example, in U.S. Patent Application Publication No. 2012/0123529, which is incorporated by reference herein in its entirety.

As noted above, the inner skirt 16 can be used to assist in suturing the leaflet structure 14 to the frame. The inner skirt 16 can have an undulating temporary marking suture to guide the attachment of the lower edges of each leaflet 40. The inner skirt 16 itself can be sutured to the struts of the frame 12 using sutures 70, as noted above, before securing the leaflet structure 14 to the skirt 16. The struts that intersect the marking suture desirably are not attached to the inner skirt 16. This allows the inner skirt 16 to be more pliable in the areas not secured to the frame and minimizes stress concentrations along the suture line that secures the lower edges of the leaflets to the skirt. As noted above, when the skirt is secured to the frame, the fibers 78, 80 of the skirt (see FIG. 12) generally align with the angled struts of the frame to promote uniform crimping and expansion of the frame.

FIG. 20 shows one specific approach for securing the commissure portions 122 of the leaflet structure 14 to the commissure window frame portions 30 of the frame. The flexible connector 124 (FIG. 19) securing two adjacent sides of two leaflets is folded widthwise and the upper tab portions 112 are folded downwardly against the flexible connector.

Each upper tab portion 112 is creased lengthwise (vertically) to assume an L-shape having an inner portion 142 folded against the inner surface of the leaflet and an outer portion 144 folded against the connector 124. The outer portion 144 can then be sutured to the connector 124 along a suture line 146. Next, the commissure tab assembly is inserted through the commissure window 20 of a corresponding window frame portion 30, and the folds outside of the window frame portion 30 can be sutured to portions 144.

FIG. 20 also shows that the folded down upper tab portions 112 can form a double layer of leaflet material at the commissures. The inner portions 142 of the upper tab portions 112 are positioned flat against layers of the two leaflets 40 forming the commissures, such that each commissure comprises four layers of leaflet material just inside of the window frames 30. This four-layered portion of the commissures can be more resistant to bending, or articulating, than the portion of the leaflets 40 just radially inward from the relatively more-rigid four-layered portion. This causes the leaflets 40 to articulate primarily at inner edges 143 of the folded-down inner portions 142 in response to blood flowing through the prosthetic valve during operation within the body, as opposed to articulating about or proximal to the axial struts of the window frames 30. Because the leaflets articulate at a location spaced radially inwardly from the window frames 30, the leaflets can avoid contact with and damage from the frame. However, under high forces, the four layered portion of the commissures can splay apart about a longitudinal axis adjacent to the window frame 30, with each inner portion 142 folding out against the respective outer portion 144. For example, this can occur when the prosthetic valve 10 is compressed and mounted onto a delivery shaft, allowing for a smaller crimped diameter. The four-layered portion of the commissures can also splay apart about the longitudinal axis when the balloon catheter is inflated during expansion of the prosthetic valve, which can relieve some of the pressure on the commissures caused by the balloon, reducing potential damage to the commissures during expansion.

After all three commissure tab assemblies are secured to respective window frame portions 30, the lower edges of the leaflets 40 between the commissure tab assemblies can be sutured to the inner skirt 16. For example, as shown in FIG. 21, each leaflet 40 can be sutured to the inner skirt 16 along suture line 154 using, for example, Ethibond Excel® PET thread. The sutures can be in-and-out sutures extending through each leaflet 40, the inner skirt 16, and each reinforcing strip 72. Each leaflet 40 and respective reinforcing strip 72 can be sewn separately to the inner skirt 16. In this manner, the lower edges of the leaflets are secured to the frame 12 via the inner skirt 16. As shown in FIG. 21, the leaflets can be further secured to the skirt with blanket sutures 156 that extend through each reinforcing strip 72, leaflet 40 and the inner skirt 16 while looping around the edges of the reinforcing strips 72 and leaflets 40. The blanket sutures 156 can be formed from PTFE suture material. FIG. 22 shows a side view of the frame 12, leaflet structure 14 and the inner skirt 16 after securing the leaflet structure 14 and the inner skirt 16 to the frame 12 and the leaflet structure 14 to the inner skirt 16.

Figure 23:
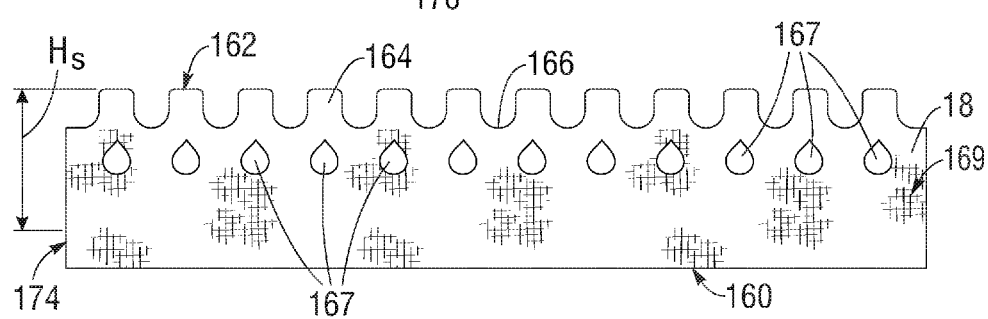
FIG. 23 shows a flattened view of an exemplary outer skirt.

FIG. 23 shows a flattened view of the outer skirt 18 prior to its attachment to the frame 12. The outer skirt 18 can be laser cut or otherwise formed from a strong, durable material such as PET or various other suitable synthetic or natural materials configured to restrict and/or prevent blood-flow therethrough. The outer skirt 18 can comprise a substantially straight lower edge 160 and an upper edge 162 defining a plurality of alternating projections 164 and notches 166, or castellations. The outer skirt 18 can also comprise a plurality of openings 167 (e.g., 12 in the illustrated embodiment) disposed on an intermediate portion 169 (i.e., the portion between the lower and upper edges 160, 162) of the outer skirt 18. The openings 167 are spaced from the lower edge 160 and the upper edge 162 such that the material of the outer skirt 18 separates the openings 167 from the lower and upper edges 160, 162.

As best shown in FIG. 3, a lower portion 174 of the outer skirt 18 can be wrapped around the inflow end 15 of the frame 12, and the lower edge 160 of the outer skirt 18 can be attached to the lower edge 176 of the inner skirt 16 and/or the frame 12 at the inflow end of the prosthetic valve 10. In some embodiments, the outer skirt 18 can be attached to the inner skirt 16, for example, with sutures or a suitable adhesive.

In lieu of or in addition to sutures, the outer skirt 18 can be attached to the inner skirt 16, for example, by ultrasonic welding. Ultrasonic welding can provide several significant advantages. For example, ultrasonic welding can be relatively less time consuming and less expensive compared to suturing, while also providing improved strength.

As shown in FIG. 1, each projection 164 of the outer skirt 18 can be attached to the third row III of struts 26 (FIG. 5) of the frame 12. The upper edges 162 of the projections 164 can, for example, be wrapped over respective struts 26 of row III and secured with sutures 168.

As can be seen in FIGS. 1-3, the outer skirt 18 is secured to the frame 12 such that when the frame is in its expanded configuration (e.g., when deployed in a subject), there is excess material between the lower edge 160 and the upper edge 162 that does not lie flat against the outer surface of the frame 12. The outer skirt 18 can be secured directly to frame 12 and/or indirectly to frame 12, for example, by securing the outer skirt 18 to the inner skirt 16, which is directly secured to the frame 12. In the expanded configuration of the prosthetic valve, the distance between the upper and lower attachment points of the outer skirt 18 decreases (foreshortens), resulting in radial expansion of the outer skirt 18. Additionally, the excess material between the lower and upper edges of the outer skirt 18 allows the frame 12 to elongate axially when crimped without any resistance from the outer skirt 18.

The outer skirt 18 can comprise an axial length or height $H_s$, where $H_s$ is the height of the outer skirt 18, less the lower portion 174 that is wrapped around the inflow end 15 of the frame 12, as best shown in FIGS. 1, 3, and 23. In some embodiments, the height $H_s$ can be substantially the same as the axial length between the upper attachment point of the outer skirt 18 to the frame 12 and the inflow end 15 of the frame 12 when the frame 12 is fully crimped. In such embodiments, when the frame 12 is fully crimped, the outer skirt 18 can lie flat against the outer surface of the frame 12. In other embodiments, the height $H_s$ of the outer skirt 18 can exceed the axial length between the upper attachment point of the outer skirt 18 to the frame 12 and the inflow end 15 of the frame 12 when the frame 12 is fully crimped. In such embodiments, the outer skirt 18 can comprise a plurality of creases 170 (e.g., twelve in the illustrated embodiment).

As best shown in FIG. 3, the creases 170 can extend axially from the lower edge 160 toward the intermediate portion 169 of the outer skirt 18. The creases 170 can be aligned circumferentially with respective projections 164, and the outer skirt 18 can be oriented with respect to the frame 12 such that the creases 170 are circumferentially aligned between a respective pair of apices 22a (FIG. 5) that are formed by the struts 22 at the inflow end 15 of the frame 12. For example, the creases 170 can be circumferentially aligned along a respective vertical line 172 (FIGS. 2 and 5) that is parallel to the longitudinal axis of the frame 12 and bisects the frame 12 at a location equidistant from each apex 22a of a respective pair of apices 22a. In this manner, the creases 170 can cause excess material of the outer skirt 18 to retract radially inwardly between the apices 22a and into the inflow end 15 of the frame 12 when the prosthetic valve 10 is crimped from the expanded configuration. As best shown in FIG. 2, each crease 170 can be circumferentially aligned with a respective opening 167 and projection 164 along a respective line 172.

Figure 28:
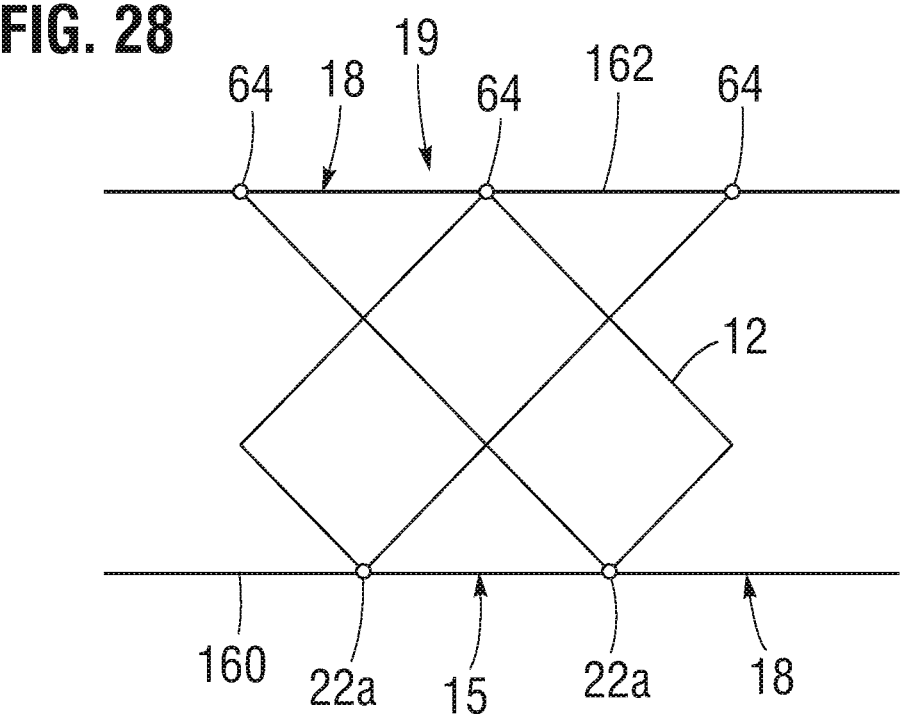
FIG. 28 shows a schematic view of a portion of the frame and the outer skirt of the prosthetic valve of FIG. 1 with the frame in an expanded configuration.
Figure 29:
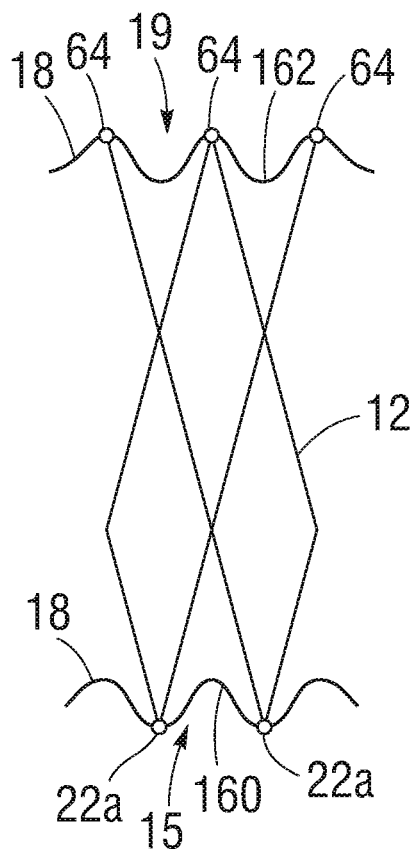
FIG. 29 shows a schematic view of the frame and the outer skirt of FIG. 28 with the frame in a collapsed configuration.

Referring to FIGS. 28-29, in lieu of or in addition to the creases 170 (FIG. 1), the outer skirt 18 can be attached and/or positioned relative to the frame 12 such that the lower edge 160 of the outer skirt 18 contacts the inflow end 15 of the frame 12 at locations (e.g., apices 22a) that are offset relative to locations (e.g., the junctions 64) that the upper edge 162 of the outer skirt 18 contacts the outflow end 19 of the frame 12. Configuring the outer skirt 18 and the frame 12 in this manner can cause excess material of the outer skirt 18 to retract inwardly between the apices 22a of the frame 12 when the prosthetic valve 10 is crimped from the expanded configuration (e.g., FIG. 28) to the collapsed configuration (e.g., FIG. 29), as shown in FIG. 29.

This configuration also spreads the deformed fabric of the collapsed outer skirt 18 over a relatively large distance, which reduces the amount of outer skirt material per cross sectional area and flattens the outer skirt 18 around the crimped frame 12, thus reducing the crimped profile of the prosthetic heart valve 10. Reducing the crimped profile of the prosthetic heart valve 10 can reduce the push force necessary to move the prosthetic heart valve 10 relative to a patient's vasculature or a delivery cylinder of a delivery apparatus. It can also reduce the compression force that is exerted upon the leaflets 40 to achieve a particular crimp profile, which can reduce and/or eliminate damage to the leaflets 40 caused by over compressing the leaflets 40 during crimping and/or delivery of the prosthetic heart valve 10 to an implantation location.

Retracting the excess material within the frame 12 below the leaflets 40 when the prosthetic valve 10 is crimped advantageously allows the prosthetic valve 10 to have a relatively large outer skirt 18, which can significantly reduce perivalvular leakage, while minimizing the radial crimp profile of the prosthetic valve 10. For example, the height $H_s$ of the outer skirt 18 can be about 9 mm to about 25 mm or about 13 mm to about 20 mm, with about 19 mm being a specific example. The height $H_f$ of the frame 12 in the radially expanded state can be about 12 mm to about 27 mm or about 15 mm to about 23 mm, with about 20 mm being a specific example. The outer skirt 18 can be sized such that a ratio $H_s:H_f$, where $H_s$ (FIG. 23) is the height of the outer skirt 18, and $H_f$ (FIG. 5) is the height of the frame 12 in the expanded state, can be between about 0.75 to about 0.95. In some embodiments, the ratio $H_s:H_f$ can be between about 0.80 to about 0.90 or about 0.84 to about 0.87. In one particular embodiment, the ratio $H_s:H_f$ can be 0.86.

Providing a relatively larger outer skirt 18 allows the prosthetic valve 10 to be positioned in a wider range of positions relative to the native annulus, while providing adequate perivalvular sealing. This improved range can make the prosthetic valve 10 easier to position during the implantation procedure. It also allows the prosthetic valve to adapt to greater variation in native annulus anatomy.

In addition, the creases 170 can assist the outer skirt 18 in collapsing in a predetermined, uniform manner when the prosthetic valve is crimped. This uniformity can prevent the outer skirt 18 from bunching or wadding when crimping and/or loading the prosthetic valve 10 in a delivery apparatus, which in turn allows the outer skirt 18 to expand to its functional state more quickly and consistently when deploying the prosthetic valve 10, as further described below.

Each crease 170 can be formed, for example, by overlapping adjacent portions of the outer skirt 18 and securing them together. The creases can then be secured in the overlapped state, for example, by sutures, ultrasonic welding, and/or an adhesive. The creases 170 can be referred to as permanent creases in that the creases are retained when the prosthetic valve 10 is in a radially compressed state and a radially expanded state.

As best shown in FIG. 23, the openings 167 can be laterally (circumferentially in FIGS. 1-3) spaced apart relative to adjacent openings 167 and be laterally (circumferentially in FIGS. 1-3) aligned with a respective projection 164. The openings 167 can also be circumferentially aligned with respective creases 170, as best shown in FIGS. 1 and 3. For example, the projections 164, the openings 167, and the creases 170 can be aligned along the respective vertical lines 172, as best shown in FIG. 2. Aligning the openings 167 and the creases 170 can, for example, allow blood to quickly enter, and thus expand, the overlapped portions of the outer skirt 18 when the prosthetic valve is initially deployed, as further described below.

The openings 167 can also advantageously allow back-flowing blood (e.g., retrograde blood) to enter the outer skirt 18 from a different angle or direction than the notches 166, thus improving how quickly the outer skirt 18 initially expands and improving perivalvular sealing. The openings 167 can be provided in lieu of or in addition to the notches 166.

The openings 167 can comprise various shapes. For example, the openings 167 can comprise a tear-drop shape, as shown in the illustrated embodiment. In other embodiments, the openings can be circular, elliptical, rectangular, etc.

The prosthetic valve 10 can be configured for and mounted on a suitable delivery apparatus for implantation in a subject. Several catheter-based delivery apparatuses are known; a non-limiting example of a suitable catheter-based delivery apparatus includes that disclosed in U.S. Patent Application Publication No. 2013/0030519, which is incorporated by reference herein in its entirety, and U.S. Patent Application Publication No. 2012/0123529.

To implant a plastically-expandable prosthetic valve 10 within a patient, the prosthetic valve 10 including the outer skirt 18 can be crimped on an elongated shaft 180 of a delivery apparatus, as best shown in FIG. 14. The prosthetic valve, together with the delivery apparatus, can form a delivery assembly for implanting the prosthetic valve 10 in a patient's body. The shaft 180 comprises an inflatable balloon 182 for expanding the prosthetic valve within the body. With the balloon 182 deflated, the prosthetic valve 10 can then be percutaneously delivered to a desired implantation location (e.g., a native aortic valve region). Once the prosthetic valve 10 is delivered to the implantation site (e.g., the native aortic valve) inside the body, the prosthetic valve 10 can be radially expanded to its functional state by inflating the balloon 182.

When the prosthetic valve 10 expands, the notches 166 and the openings 167 allow blood to flow between the outer skirt 18 and the inner skirt 16. This blood-flow causes the excess fabric of the outer skirt 18 to further radially expand and separate from the inner skirt 16.

The expanded outer skirt 18 can fill-in gaps between the frame 12 and the surrounding native annulus to assist in forming a good, fluid-tight seal between the prosthetic valve 10 and the native annulus. The outer skirt 18 therefore cooperates with the inner skirt 16 to avoid perivalvular leakage after implantation of the prosthetic valve 10. In several embodiments, the prosthetic valve 10 comprising the outer skirt 18 that expands radially outwardly can have reduced perivalvular leakage when implanted in a subject compared to a similar prosthetic valve that has a relatively smaller outer skirt or lacks the outer skirt 18.

Alternatively, a self-expanding prosthetic valve 10 can be crimped to a radially collapsed configuration and restrained in the collapsed configuration by inserting the prosthetic valve 10, including the outer skirt 18, into a sheath or equivalent mechanism of a delivery catheter. The prosthetic valve 10 can then be percutaneously delivered to a desired implantation location. Once inside the body, the prosthetic valve 10 can be advanced from the delivery sheath, which allows the prosthetic valve to expand to its functional state.

When the outer skirt 18 is exposed from the delivery sheath, the notches 166 and the openings 167 allow blood to flow between the outer skirt 18 and the inner skirt 16. This blood-flow causes the excess fabric of the outer skirt 18 to further radially expand and separate from the inner skirt 16.

Figure 24:
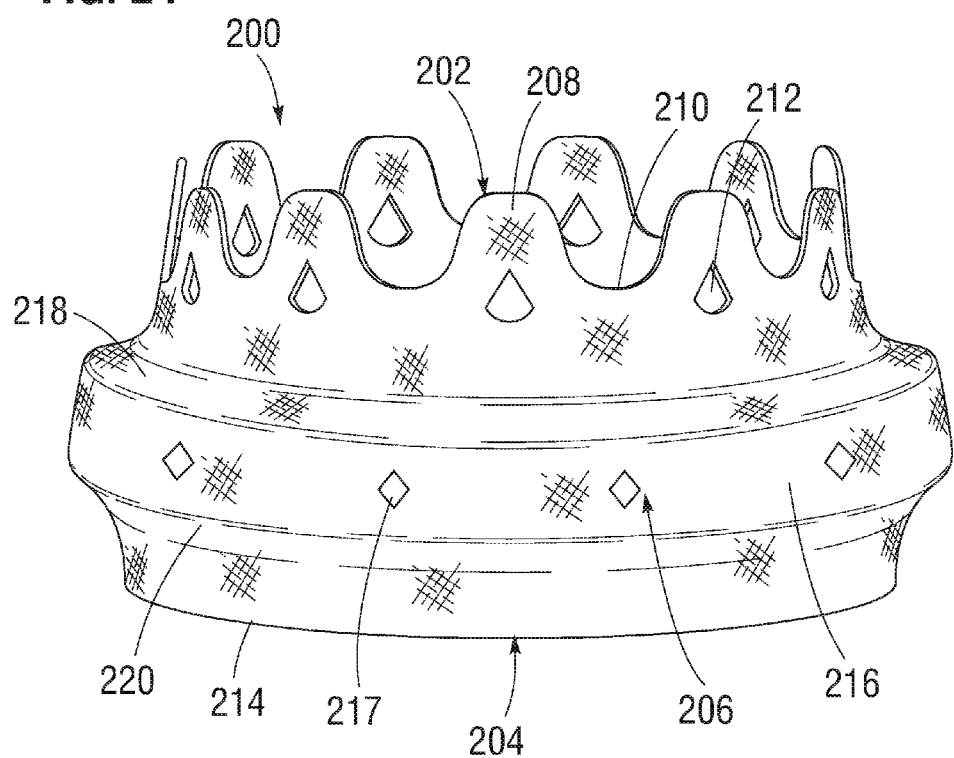
FIG. 24 shows another exemplary embodiment of an outer skirt.

FIG. 24 shows an exemplary embodiment of an outer skirt 200. The outer skirt 200 can comprise a first end portion 202 (i.e., the upper end portion as depicted in FIG. 24), a second end portion 204 (i.e., the lower end portion as depicted in FIG. 24), and an intermediate portion 206 disposed between the first and second end portions 202, 204.

The first end portion 202 of the outer skirt 200 can include a plurality of alternating projections 208 and notches 210 and can also include a plurality of first openings 212. The first end portion 202 can be configured similar to the projections 164, the notches 166, and the openings 167 of the outer skirt 18. For example, the first openings 212 can be circumferentially aligned with the projections 208 and circumferentially offset relative to the notches 210. The first end portion 202 can be attached to an inner skirt and/or frame of a prosthetic heart valve, as further described below.

The first openings 212 can comprise various sizes and/or shapes. For example, as shown in FIG. 24, the first openings 212 comprise a "tear-drop" shape. In other embodiments, the first openings 212 can be larger (e.g., elongate) or smaller and can comprise various other shapes (e.g., circular, rectangular, or ovular) than those shown in the illustrated embodiment.

The first end portion 202 of the outer skirt 200 can comprise first outer diameter. In some embodiments, the first, outer diameter of the first end portion 202 is at least substantially similar to a second, outer diameter of the second end portion 204 and smaller than a third, outer diameter of the intermediate portion 206. In other embodiments, the first diameter of the first end portion 202 can be smaller than the second diameter of the second end portion 204 and the third diameter of the intermediate portion 206. In yet other embodiments, the first diameter of the first end portion 202 can be larger than the second diameter of the second end portion 204 and can be smaller than the third diameter of the intermediate portion 206.

The second end portion 204 of the outer skirt 200 can comprise a substantially straight lower edge 214. The second end portion 204 can be attached to an inner skirt and/or frame of a prosthetic heart valve, as further described below.

The second diameter of the second end portion can be smaller than the third diameter of the intermediate portion 206.

The intermediate portion 206 of the outer skirt 200 can comprise a bulge extending radially outwardly to the third diameter relative to the first and second end portions 202, 204. The intermediate portion 206 can comprise a radially outwardly facing surface 216. As shown, in some embodiments, the surface 216 can be relatively flat. In other embodiments, the surface 216 can be relatively tapered, from the first end portion 202 to the second end portion 204, or vice versa. In yet other embodiments, the surface 216 can be relatively curved or rounded.

In some embodiments, the surface 216 of the intermediate portion 206 can comprise a plurality of second openings 217. The second openings 217 can be spaced apart relative to each other, circumferentially aligned with the notches 210 of the first end portion 202, and circumferentially offset relative to the first openings 212 and the projections 208 of the first end portion 202. The second openings 217 can comprise various shapes and/or sizes, including diamond-shaped (as shown in FIG. 24), circular, rectangular, ovular, etc. In alternative embodiments, the surface 216 can be formed without the second openings 217.

The intermediate portion 206 can also comprise first and second transition sections 218, 220 separated relative to each other by the surface 216 and disposed adjacent to the first and second end portions 202, 204, respectively. In some embodiments, the transition sections 218, 220 can be at least substantially perpendicular to the surface 216. In such embodiments, the outer diameter of the outer skirt 200 abruptly transitions from the respective first and second diameters of the first and second end portions 202, 204 to the third diameter of the intermediate portion 206 in a step- or flange-like manner. In other embodiments, the transition sections 218, 220 can be angled between the respective end portions 202, 204 and the surface 216 such that the outer diameter of the outer skirt 200 tapers from the respective first and second diameters of the end portions 202, 204 to the third diameter of the intermediate portion 206.

The outer skirt 200 can be coupled to a frame and/or an inner skirt of a prosthetic heart valve similar to the manner in which the outer skirt 18 is coupled to the frame 12 and/or the inner skirt 16 of the prosthetic heart valve 10. For example, the outer skirt 200 can be attached to a frame and/or inner skirt of a prosthetic heart valve by sutures and/or ultrasonic welding.

The outer skirt 200 can be formed of materials such as PET, PTFE, ePTFE, polyurethane, polyester, and/or other suitable materials configured to restrict and/or prevent blood-flow therethrough. In some embodiments, the outer skirt 200 can be formed from a generally flat strip (e.g., similar to the outer skirt 18 as shown in FIG. 23) and formed into a tube by welding the ends together, as shown in FIG. 24. In other embodiments, the outer skirt 200 formed by weaving the outer skirt 200 into a tubular shape. The bulge in the intermediate portion 206 can be formed, for example, by shape-setting the material to a desired configuration (e.g., as shown in FIG. 24).

The outer skirt 200 can be configured to be radially compressed to a delivery configuration and to radially expand from the delivery configuration to a function configuration, in a manner similar to the outer skirt 18. In some embodiments, the outer skirt 200 can be self-expandable, such as by including Nitinol threads in the outer skirt 200. Additionally or alternatively, the outer skirt 200 can be expanded by blood flowing into the outer skirt 200 through the notches 210 and/or the openings 212.

In this manner, the outer skirt 200 in conjunction with the inner skirt 16 can reduce and/or eliminate perivalvular leakage between a frame of a prosthetic heart valve and a native annulus. As a result, the outer skirt 200 can improve functionality of a prosthetic heart valve and thus improve functionality of a patient's heart.

Figure 25:
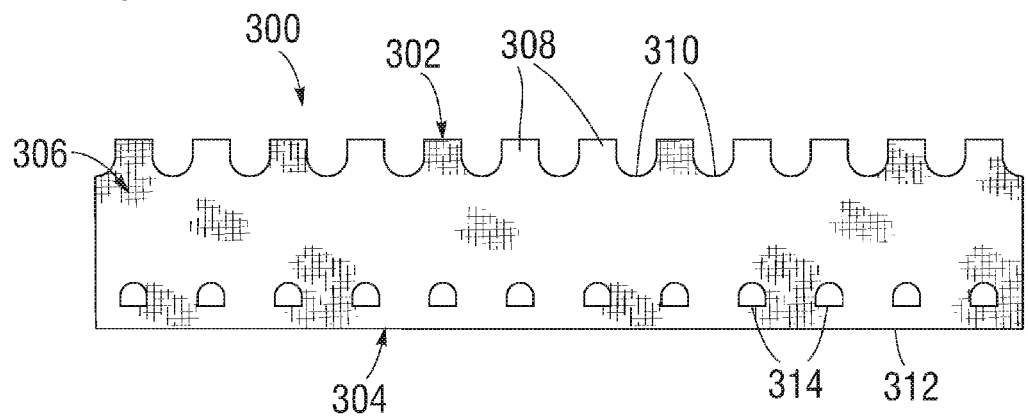
FIGS. 25-27 show various views of another exemplary embodiment of an outer skirt.
Figure 26:
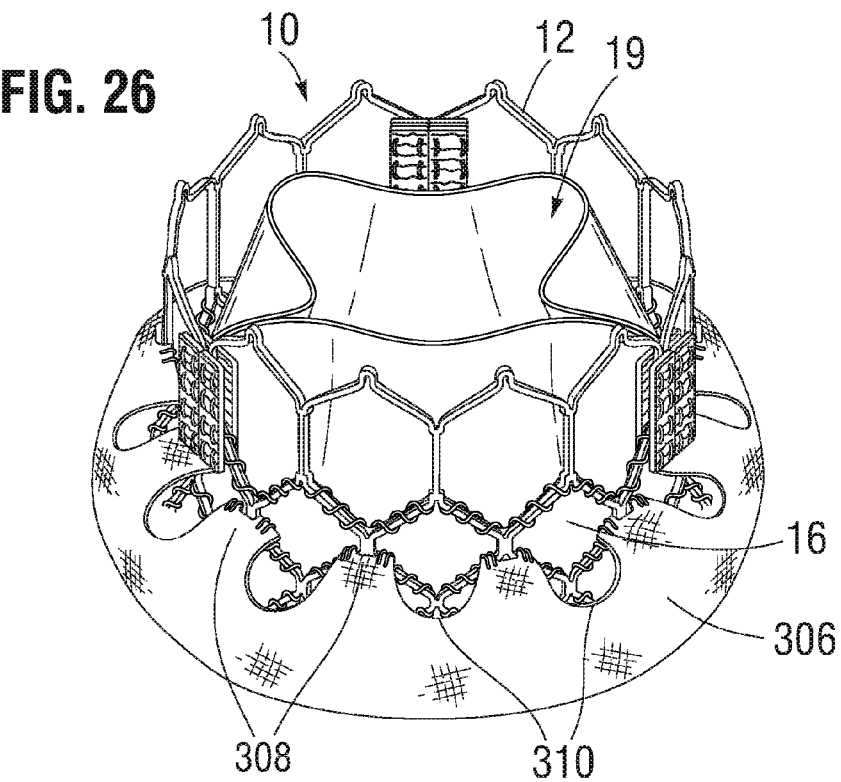
Figure 27:
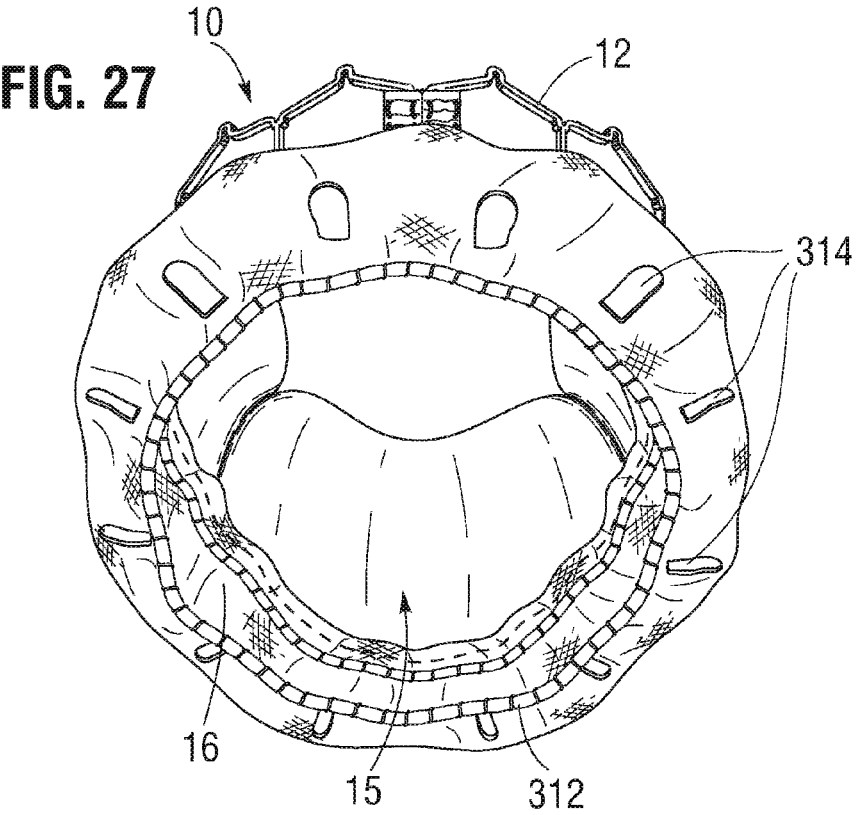

FIGS. 25-27 show an exemplary embodiment of an outer skirt 300. FIG. 25 shows a flattened view of the outer skirt 300 prior to its attachment to a prosthetic heart valve. FIGS. 26-27 show the outer skirt 300 attached to the prosthetic heart valve 10 in lieu of outer skirt 18.

Referring to FIG. 25, the outer skirt 300 can comprise a first end portion 302 (i.e., the upper end portion as depicted in FIG. 25), a second end portion 304 (i.e., the lower end portion as depicted in FIG. 25), and an intermediate portion 306 disposed between the first and second end portions 302, 304. The first end portion 302 of the outer skirt 300 can include a plurality of alternating projections 308 and notches 310, or castellations. The second end portion 304 of the outer skirt 300 can comprise a substantially straight lower edge 312 and can have a plurality of openings 314. In some embodiments, the openings 314 can be laterally spaced apart relative to each other and laterally aligned with the projections 308 of the first end portion 302 and laterally offset relative to the notches 310 of the first end portion 302. Alternatively, the openings 314 can be laterally aligned with the notches 310 of the first end portion 302 and laterally offset relative to the projections 308, or some combination of alignment with either the projections 308, the notches 310 or neither one. The openings 314 can comprise various sizes and/or geometric shapes, including circular, ovular, rectangular, and/or combinations of shapes.

Referring to FIG. 26, the projections 308 of the first end portion 302 can be attached to the inner skirt 16 and/or the frame 12 of the prosthetic heart valve 10 using sutures (as shown) and/or ultrasonic welding. As shown in FIG. 27, the lower edge 312 of the second end portion 304 can be attached to the inner skirt 16 and/or the frame 12 of the prosthetic heart valve 10 using sutures (as shown) and/or ultrasonic welding.

The outer skirt 300 can be formed of materials such as PET, PTFE, ePTFE, polyurethane, polyester, and/or other suitable materials configured to restrict and/or prevent blood-flow therethrough.

The outer skirt 300 can reduce and/or eliminate perivalvular leakage when the prosthetic heart valve 10 is implanted in a native heart valve annulus (e.g., a native aortic valve annulus or a native mitral valve annulus). For example, blood flowing from the inflow end portion 15 (FIG. 27) toward the outflow end portion 19 (FIG. 26) of the prosthetic heart valve 10 (i.e., antegrade blood flow) can enter the outer skirt 300 through the openings 314 of the second end portion 304, as best shown FIG. 27. Similarly, blood flowing from the outflow end portion 19 toward the inflow end portion 15 of the prosthetic heart valve 10 (i.e., retrograde blood flow) can enter the outer skirt 300 through the notches 310 of the first end portion 302, as best shown in FIG. 26. In those embodiments where the openings 314 and the notches 310 are circumferentially offset relative to each other, the blood-flow entering the openings 314 and/or the notches 310 cannot pass directly through the outer skirt 300. The outer skirt 300 expands radially outwardly and seals and/or reduces gaps between the prosthetic heart valve 10 and the native annulus, thereby reducing and/or eliminating perivalvular leakage in conjunction with the inner skirt 16.

Figure 30:
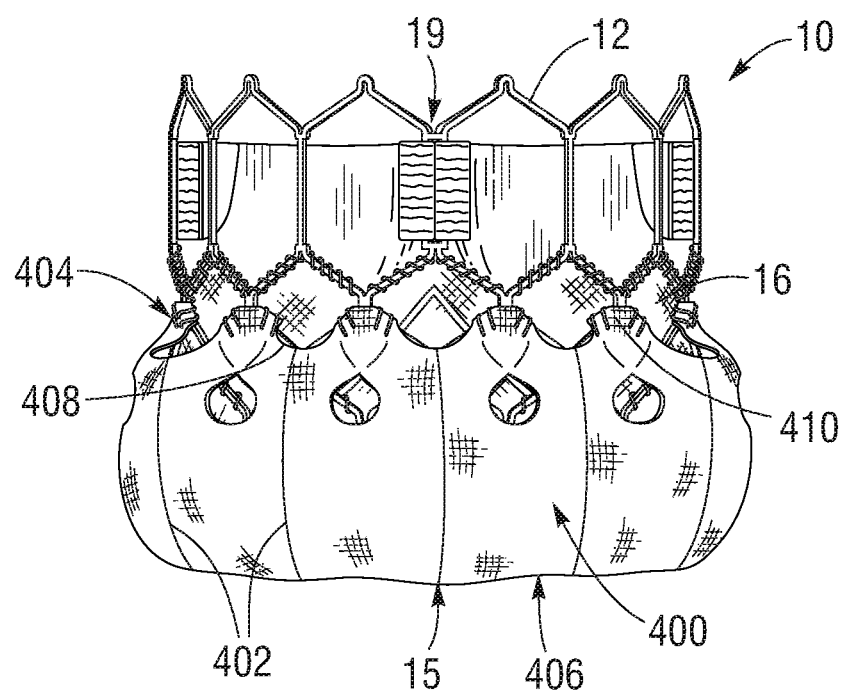
FIG. 30 shows another exemplary embodiment of an outer skirt.

FIG. 30 shows an exemplary embodiment of an outer skirt 400. The outer skirt 400 can be configured similar to the outer skirt 18 of the prosthetic heart valve 10 and can be attached to the prosthetic heart valve 10 in a manner similar to the outer skirt 18. In some embodiments and in lieu of or in addition to creases at the inflow end portion 15 of the prosthetic heart valve 10 (e.g., the creases 170 of the outer skirt 18), the outer skirt 400 can have creases 402 extending axially from a first end portion 404 of the outer skirt 400 to a second end portion 406 of the outer skirt 400. The creases 402 can be circumferentially aligned with notches 408 and circumferentially offset relative to projections 410 of the first end portion 404.

In this manner, the outer skirt 400 can expand from a compressed configuration to an expanded configuration (and vice versa) in a uniform and/or predictable manner, similar to a bellows or an accordion. As a result, the creases 402 facilitate uniform crimping and/or expansion and/or reduce the crimped radial profile of a prosthetic heart valve in compressed delivery configuration.

In some embodiments, the outer skirt 400 can comprise one or more reeds or valves configured to allow blood to flow into and/or through the outer skirt 400. For example, the outer skirt 400 can comprise a flap that is configured to selectively allow blood to flow into and/or through the outer skirt 400.

The outer skirt 400 can be formed, for example, by shape setting the outer skirt in this manner. In some embodiments, the creases 402 can be formed by ultrasonic welding.

It should be noted that, in some embodiments, the outer skirts 200, 300 can comprise creases similar to the creases 170, 402 of the outer skirt 18. The creases can be configured to facilitate uniform crimping and/or expansion and/or to reduce the crimped radial profile of a prosthetic heart valve in compressed delivery configuration. In some embodiments, the creases can be formed by ultrasonic welding.

It should also be noted that the features of any embodiment can be combined with one or more of the features of any other embodiment or embodiments. For example, in some embodiments, an outer skirt can comprise the creases 170 of the outer skirt 18 and the creases 402 of the outer skirt 400.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope of these claims.

We claim:

1. An implantable prosthetic valve comprising:
   an annular frame comprising an inflow end and an outflow end and being radially collapsible and expandable between a radially collapsed configuration and a radially expanded configuration, the frame defining an axial direction extending from the inflow end to the outflow end;
   a leaflet structure positioned within the frame and secured thereto; and
   an annular outer skirt positioned around an outer surface of the frame, wherein the outer skirt comprises:
      an inflow edge secured to the frame at a first location;

an outflow edge comprising a plurality of alternating projections and notches, wherein the projections are secured to the frame at a second location, and the notches are not directly secured to the frame;

an intermediate portion between the inflow edge and the outflow edge that comprises a plurality of openings; and a plurality of axially extending creases, wherein each of the openings of the outer skirt is circumferentially aligned with a respective crease of the outer skirt.

2. The prosthetic valve of claim 1, wherein when the frame is in the collapsed configuration, the axial distance between the inflow edge of the outer skirt and the outflow edge of the outer skirt is greater than when the valve is in the expanded configuration, increasing tension of the intermediate portion of the outer skirt.

3. The prosthetic valve of claim 1, wherein the outer skirt comprises a first height, and the frame in the radially expanded configuration comprises a second height, and wherein a ratio of the first height to the second height about 0.75 to about 0.95.

4. The prosthetic valve of claim 3, wherein the ratio of the first height to the second height is 0.86.

5. The prosthetic valve of claim 1, wherein the creases are formed by suturing portions of the outer skirt to each other.

6. The prosthetic valve of claim 1, wherein the creases are formed by ultrasonic welding portions of the outer skirt to each other.

7. The prosthetic valve of claim 1, wherein each of the creases of the outer skirt is circumferentially aligned with a respective projection of the outer skirt.

8. The prosthetic valve of claim 1, wherein the outer skirt is positioned relative to the frame such that each of the creases of the outer skirt is circumferentially positioned between a respective pair of apices formed by struts at the inflow end of the frame.

9. The prosthetic valve of claim 8, wherein each of the creases is positioned equidistantly between a respective pair of apices.

10. The prosthetic valve of claim 1, further comprising an annular inner skirt positioned around an inner surface of the frame, wherein the inner skirt comprises an inflow edge secured to the frame at a third location, an outflow edge secured to the frame at a fourth location.

11. The prosthetic valve claim 10, wherein the inflow edge of the outer skirt is attached to the inflow edge of the inner skirt.

12. The prosthetic valve of claim 11, wherein the inflow edge of the outer skirt is attached to the inflow edge of the inner skirt with sutures.

13. The prosthetic valve of claim 11, wherein the inflow edge of the outer skirt is attached to the inflow edge of the inner skirt by ultrasonic welding.

14. The prosthetic valve of claim 1, wherein at least a portion of the outer skirt is configured to retract radially within the frame when the frame is the radially collapsed configuration.

15. The prosthetic valve of claim 1, wherein the outer skirt is configured such that blood can flow through the openings and the notches of the outer skirt and blood can flow through a space between the outer skirt and the frame.

16. The prosthetic valve of claim 1, wherein the outer skirt is attached to the frame such that each of the projections of the outer skirt is circumferentially positioned between a respective pair of apices formed by struts at the inflow end of the frame.

17. An implantable prosthetic valve comprising:
an annular frame comprising an inflow end and an outflow end and being radially collapsible and expandable between a radially collapsed configuration and a radially expanded configuration, the frame defining an axial direction extending from the inflow end to the outflow end;
a leaflet structure positioned within the frame and secured thereto; and
an annular outer skirt positioned around an outer surface of the frame, wherein the outer skirt comprises:
an inflow edge secured to the frame at a first location;
an outflow edge comprising a plurality of alternating projections and notches, wherein the projections are secured to the frame at a second location, and the notches are not directly secured to the frame;
an intermediate portion between the inflow edge and the outflow edge that comprises a plurality of openings; and
a plurality of axially extending creases, wherein each of the creases of the outer skirt is circumferentially aligned with a respective projection of the outer skirt.

18. An implantable prosthetic valve comprising:
an annular frame comprising an inflow end and an outflow end and being radially collapsible and expandable between a radially collapsed configuration and a radially expanded configuration, the frame defining an axial direction extending from the inflow end to the outflow end;
a leaflet structure positioned within the frame and secured thereto; and
an annular outer skirt positioned around an outer surface of the frame, wherein the outer skirt comprises:
an inflow edge secured to the frame at a first location;
an outflow edge comprising a plurality of alternating projections and notches, wherein the projections are secured to the frame at a second location, and the notches are not directly secured to the frame;
an intermediate portion between the inflow edge and the outflow edge that comprises a plurality of openings; and
a plurality of axially extending creases, wherein the outer skirt is positioned relative to the frame such that each of the creases of the outer skirt is circumferentially positioned between a respective pair of apices formed by struts at the inflow end of the frame; wherein each of the creases of the outer skirt is circumferentially aligned with a respective projection of the outer skirt.

19. The prosthetic valve of claim 18, wherein each of the creases is positioned equidistantly between a respective pair of apices.

20. An implantable prosthetic valve comprising:
an annular frame comprising an inflow end and an outflow end and being radially collapsible and expandable between a radially collapsed configuration and a radially expanded configuration, the frame defining an axial direction extending from the inflow end to the outflow end;
a leaflet structure positioned within the frame and secured thereto; and
an annular outer skirt positioned around an outer surface of the frame, wherein the outer skirt comprises:
an inflow edge secured to the frame at a first location;
an outflow edge comprising a plurality of alternating projections and notches, wherein the projections are secured to the frame at a second location, and the notches are not directly secured to the frame; and an intermediate portion between the inflow edge and the outflow edge that comprises a plurality of openings, wherein the outer skirt comprises a first height, and the frame in the radially expanded configuration comprises a second height, and wherein a ratio of the first height to the second height is 0.75 to 0.95 wherein the outer skirt comprises a plurality of axially extending creases, wherein each of the creases of the outer skirt is circumferentially aligned with a respective projection of the outer skirt.

21. The prosthetic valve of claim 20, wherein the ratio of the first height to the second height is 0.86.

22. The prosthetic valve of claim 20, wherein the outer skirt is positioned relative to the frame such that each of the creases of the outer skirt is circumferentially positioned between a respective pair of apices formed by struts at the inflow end of the frame.

23. The prosthetic valve of claim 22, wherein each of the openings of the outer skirt is circumferentially aligned with a respective crease of the outer skirt, and wherein each of the creases of the outer skirt is circumferentially aligned with a respective projection of the outer skirt.

* * * * *